United States Patent
Xiong et al.

(10) Patent No.: US 11,466,036 B2
(45) Date of Patent: Oct. 11, 2022

(54) BORATE OF AZETIDINE DERIVATIVE

(71) Applicant: Chia Tai Tianqing Pharmaceutical Group Co., Ltd., Lianyungang (CN)

(72) Inventors: Jian Xiong, Shanghai (CN); Cheng Xie, Shanghai (CN); Xiongbin Xu, Shanghai (CN); Kevin X Chen, Shanghai (CN); Jian Li, Shanghai (CN); Shuhui Chen, Shanghai (CN); Aiming Zhang, Lianyungang (CN); Xiquan Zhang, Lianyungang (CN); Xin Tian, Lianyungang (CN)

(73) Assignee: Chia Tai Tianqing Pharmaceutical Group Co., Ltd., Lianyungang (CN)

( * ) Notice: Subject to any disclaimer, the term of this patent is extended or adjusted under 35 U.S.C. 154(b) by 0 days.

(21) Appl. No.: 17/263,476

(22) PCT Filed: Aug. 2, 2019

(86) PCT No.: PCT/CN2019/098990
§ 371 (c)(1),
(2) Date: Jan. 26, 2021

(87) PCT Pub. No.: WO2020/025037
PCT Pub. Date: Feb. 6, 2020

(65) Prior Publication Data
US 2021/0163507 A1 Jun. 3, 2021

(30) Foreign Application Priority Data

Aug. 2, 2018 (CN) .......................... 201810872672.X
Aug. 28, 2018 (CN) .......................... 201810989128.3

(51) Int. Cl.
*C07F 5/02* (2006.01)
(52) U.S. Cl.
CPC ............ *C07F 5/02* (2013.01); *C07B 2200/13* (2013.01)
(58) Field of Classification Search
CPC ...................................................... C07F 5/025
See application file for complete search history.

(56) References Cited

U.S. PATENT DOCUMENTS 11,014,943 B2 * 5/2021 Xiong ..................... A61P 35/00

FOREIGN PATENT DOCUMENTS

| CN | 101638414 A | 2/2010 |
| CN | 105732683 A | 7/2016 |
| WO | WO 2006/086600 A1 | 8/2006 |
| WO | WO 2012/177835 A1 | 12/2012 |
| WO | WO 2018/157820 A1 | 9/2018 |

OTHER PUBLICATIONS

Lei, Meng et al., "Design, synthesis, in vitro and in vivo evaluation, and structure-activity relationship (SAR) discussion of novel dipeptidyl boronic acid for the treatment of multiple myeloma and mechanism studies" Bioorganic & Medicinal Chemistry, Jun. 2018, pp. 3975-3981, vol. 26, No. 14.
Zhu, Yongqiang et al., "Design, synthesis, biological evaluation, and structure-activity relationship (SAR) discussion of dipeptidyl boronate proteasome inhibitors, Part I: comprehensive understanding of the SAR of α-amino acid boronates" J. Med. Chem., 2009, pp. 4192-4199, vol. 52.
International Search Report for PCT/CN2019/098990 dated Nov. 4, 2019.

* cited by examiner

*Primary Examiner* — Golam M Shameem
(74) *Attorney, Agent, or Firm* — Knobbe Martens Olson & Bear LLP

(57) ABSTRACT

A borate compound of an azetidine derivative, relating in particular to a compound represented by formula (I) or a pharmaceutically acceptable salt thereof, a tautomer thereof, a stereoisomer thereof or a geometric isomer thereof, as well as a use thereof in the preparation of a drug used for the treatment or prevention of multiple myeloma.

(I)

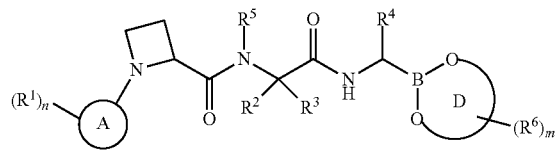

20 Claims, 1 Drawing Sheet

BORATE OF AZETIDINE DERIVATIVE

CROSS-REFERENCE TO RELATED APPLICATIONS

This application is a U.S. National Phase Application of PCT International Application Number PCT/CN2019/098990, filed on Aug. 2, 2019, designating the United States of America and published in the Chinese language, which is an International Application of and claims the benefit of priority to Chinese Patent Application No. 201810872672.X, filed on Aug. 2, 2018, and Chinese Patent Application No. 201810989128.3, filed on Aug. 28, 2018. The disclosures of the above-referenced applications are hereby expressly incorporated by reference in their entireties.

TECHNICAL FIELD

The present application relates to a borate compound of an azetidine derivative, a preparation method thereof, a pharmaceutical composition containing the same and use of the same in treating diseases associated with multiple myeloma.

BACKGROUND

Multiple myeloma (MM) is a malignant proliferative disease of plasma cells characterized by abnormal proliferation of clonal plasma cells in the bone marrow and resulting destruction of hematopoietic function, occurrence of osteolytic lesions in the bone, and detection of monoclonal immunoglobulins or fragments thereof (M protein) in serum and/or urine, and its clinical manifestations are bone pain, anemia, hypercalcemia, impairment of renal function, infection, and hemorrhage etc. Bortezomib is a reversible proteasome inhibitor that treats multiple myeloma by promoting apoptosis of myeloma cells. However, resistance to bortezomib has developed in part of the multiple myeloma patients during long-term treatment. Therefore, there is still a need for new, safe, and highly stable drugs for the treatment of multiple myeloma.

SUMMARY

The present application provides a borate of an azetidine derivative, which is a prodrug of a boronic acid compound of an azetidine derivative and is superior to the boronic acid compound in terms of stability.

In one aspect, the present application provides a compound of formula (I), or a pharmaceutically acceptable salt thereof, a tautomer thereof, a stereoisomer thereof or a geometric isomer thereof,

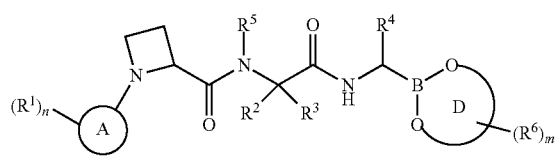

(I)

wherein, ring A is selected from the group consisting of phenyl and 5-10 membered heteroaryl; each $R^1$ is independently selected from the group consisting of halogen, CN, OH, $NH_2$, $C_{1-6}$ alkyl and $C_{1-6}$ heteroalkyl, wherein the $C_{1-6}$ alkyl or the $C_{1-6}$ heteroalkyl is optionally substituted by one or more groups selected from the group consisting of halogen, OH and $NH_2$; n is selected from the group consisting of 0, 1, 2, 3, 4 and 5; $R^2$ and $R^3$ are each independently selected from the group consisting of H and $C_{1-6}$ alkyl; $R^4$ is selected from $C_{1-6}$ alkyl; $R^5$ is selected from the group consisting of H and $C_{1-3}$ alkyl; ring D is selected from 5-10 membered heterocyclyl, wherein the 5-10 membered heterocyclyl is substituted by at least one =O; each $R^6$ is independently selected from the group consisting of halogen, OH, $NH_2$, COOH, $C_{1-6}$ alkyl, $C_{3-6}$ cycloalkyl, $C_{1-6}$ heteroalkyl, $C_{6-10}$ aryl and 5-10 membered heteroaryl, wherein the $C_{1-6}$ alkyl, $C_{3-6}$ cycloalkyl, $C_{1-6}$ heteroalkyl, $C_{6-10}$ aryl or 5-10 membered heteroaryl is optionally substituted by one or more groups selected from the group consisting of COOH, halogen, OH, N2 and SH; and m is selected from the group consisting of 0, 1, 2, 3, 4 and 5.

In some embodiments, ring A is selected from the group consisting of phenyl and 5-6 membered heteroaryl, wherein the 5-6 membered heteroaryl contains at least one ring atom selected from the group consisting of nitrogen and sulfur. In some embodiments, ring A is selected from the group consisting of phenyl, pyridinyl and thiazolyl. In some embodiments, ring A is phenyl.

In some embodiments, each $R^1$ is independently selected from the group consisting of halogen, CN, OH, $NH_2$, $C_{1-3}$ alkyl and $C_{1-3}$ alkoxy, wherein the $C_{1-3}$ alkyl or the $C_{1-3}$ alkoxy is optionally substituted by one or more groups selected from the group consisting of halogen, OH and $NH_2$. In some embodiments, each $R^1$ is independently selected from the group consisting of halogen, CN, $C_{1-3}$ alkyl, or $C_{1-3}$ alkyl substituted by one or more halogens. In some embodiments, each $R^1$ is independently selected from the group consisting of fluoro, chloro, bromo, iodo, CN, $C_{1-3}$ alkyl, or $C_{1-3}$ alkyl substituted by 1, 2 or 3 fluoro. In some embodiments, each $R^1$ is independently selected from the group consisting of fluoro, CN and trifluoromethyl. In some embodiments, each $R^1$ is independently selected from fluoro.

In some embodiments, n is selected from the group consisting of 0, 1 and 2. In some embodiments, n is selected from the group consisting of 1 and 2. In some embodiments, n is 2.

In some embodiments, the structural unit

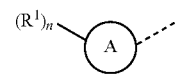

of the compound of formula (I) is selected from the group consisting of

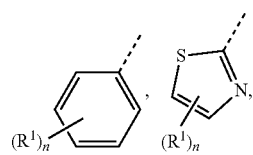

and

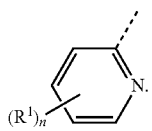

In some embodiments, the structural unit

of the compound of formula (I) is selected from the group consisting of

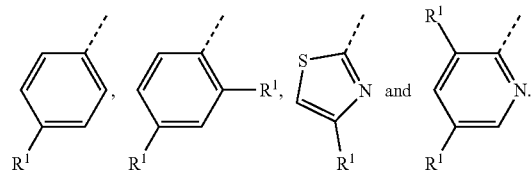

In some embodiments, the structural unit

of the compound of formula (I) is selected from the group consisting of

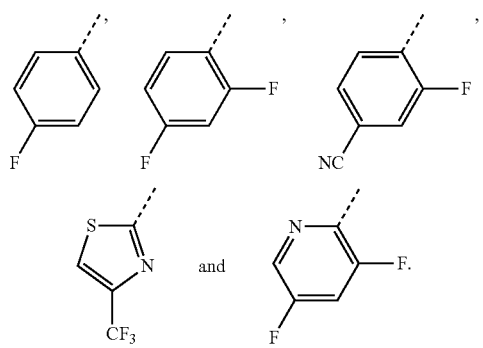

In some embodiments, the structural unit

of the compound of formula (I) is

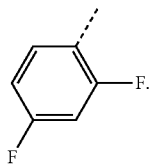

In some embodiments, $R^2$ and $R^3$ are each independently selected from the group consisting of H and $C_{1-3}$ alkyl. In some embodiments, $R^2$ and $R^3$ are each independently selected from H.

In some embodiments, $R^4$ is selected from $C_{3-5}$ alkyl. In some embodiments, $R^4$ is selected from $C_4$ alkyl. In some embodiments, $R^4$ is isobutyl.

In some embodiments, $R^5$ is selected from the group consisting of H and methyl. In some embodiments, $R^5$ is H.

In some embodiments, ring D is selected from 5-10 membered heterocyclyl, wherein the 5-10 membered heterocyclyl is substituted by one =O. In some embodiments, ring D is selected from 5-10 membered heterocyclyl, wherein ring D is

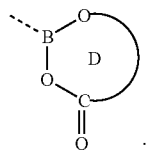

In some embodiments, ring D is selected from 5-10 membered heterocyclyl, wherein ring D is

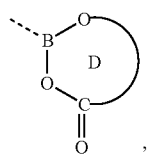

and the heteroatoms in the ring atoms of the 5-10 membered heterocyclyl include only boron and oxygen.

In some embodiments, ring D is selected from the group consisting of 5 membered heterocyclyl, 6 membered heterocyclyl and 10 membered heterocyclyl, wherein the 5 membered heterocyclyl, 6 membered heterocyclyl or 10 membered heterocyclyl is substituted at least by one =O. In some embodiments, ring D is selected from the group consisting of 5 membered heterocyclyl, 6 membered heterocyclyl and 10 membered heterocyclyl, wherein the 5 membered heterocyclyl, 6 membered heterocyclyl or 10 membered heterocyclyl is substituted by one =O. In some embodiments, ring D is selected from the group consisting of 5 membered heterocyclyl, 6 membered heterocyclyl and 10 membered heterocyclyl, wherein ring D is

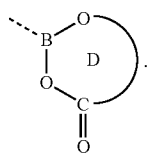

In some embodiments, ring D is selected from the group consisting of 5 membered heterocyclyl, 6 membered heterocyclyl and 10 membered heterocyclyl, wherein ring D is

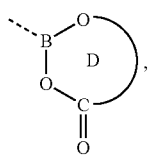

and the heteroatoms in the ring atoms of the 5 membered heterocyclyl, 6 membered heterocyclyl or 10 membered heterocyclyl include only boron and oxygen.

In some embodiments, ring D is selected from the group consisting of

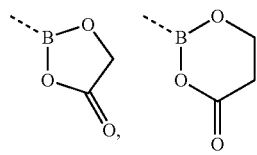 and 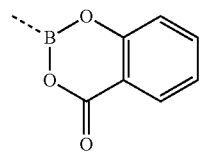

In some embodiments, ring D is

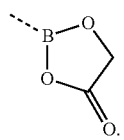

In some embodiments, m is selected from the group consisting of 0, 1, 2 and 3. In some embodiments, m is selected from the group consisting of 0, 1 and 2. In some embodiments, m is selected from the group consisting of 0 and 1.

In some embodiments, each $R^6$ is independently selected from OH, $NH_2$, COOH and $C_{1-6}$ alkyl, wherein the $C_{1-6}$ alkyl is optionally substituted by one or more groups selected from the group consisting of COOH, OH and $NH_2$. In some embodiments, each $R^6$ is independently selected from $C_{1-4}$ alkyl optionally substituted by one or more COOH. In some embodiments, each $R^6$ is independently selected from the group consisting of methyl, tert-butyl and carboxymethyl. In some embodiments, $R^6$ is carboxymethyl.

In some embodiments, the structural unit

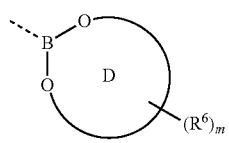

of the compound of formula (I) is

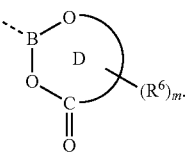

In some embodiments, the structural unit

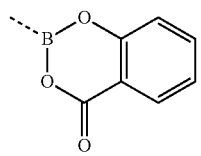

of the compound of formula (I) is selected from the group consisting of

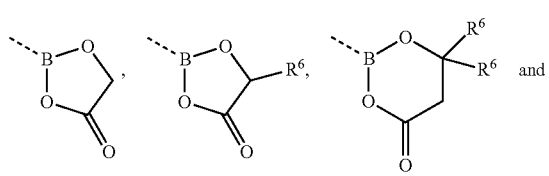

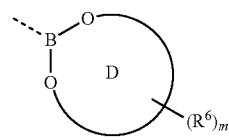

In some embodiments, the structural unit

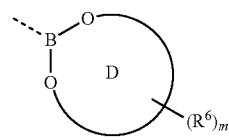

of the compound of formula (I) is selected from the group consisting of

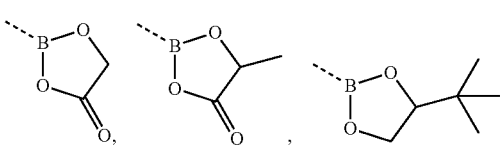

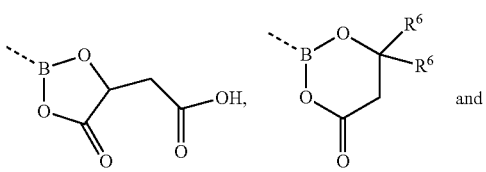

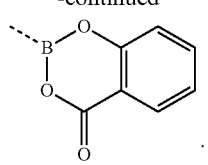

In some embodiments, the structural unit

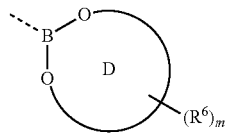

of the compound of formula (I) is

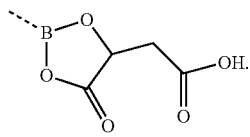

In some embodiments, the structural unit

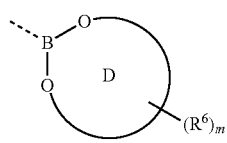

of the compound of formula (I) is selected from the group consisting of

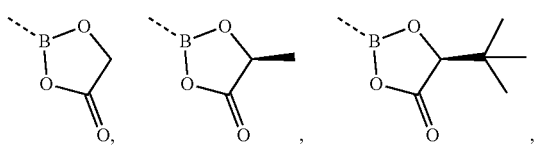

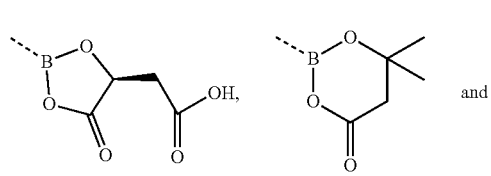

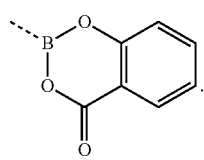

In some embodiments, the structural unit

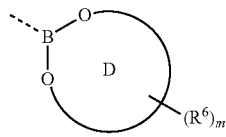

of the compound of formula (I) is

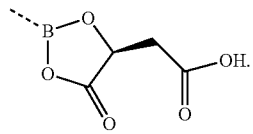

In some embodiments, the compound of formula (I) disclosed herein is a prodrug of a compound of formula (I-0),

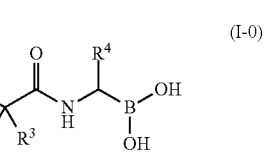

(I-0)

wherein ring A, n, $R^1$, $R^2$, $R^3$, $R^4$ and $R^5$ are as defined above for the compound of formula (I).

In some embodiments, the structural unit

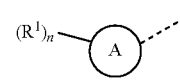

of the compound of formula (I-0) is as defined above for the compound of formula (I).

In another aspect, the present application also provides a compound of formula (I-a), or a pharmaceutically acceptable salt thereof, a tautomer thereof, a stereoisomer thereof or a geometric isomer thereof,

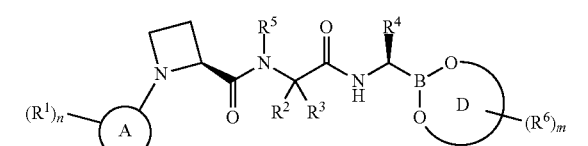

(I-a)

wherein ring A, ring D, n, $R^1$, $R^2$, $R^3$, $R^4$, $R^5$, $R^6$ and m are as defined above for the compound of formula (I).

In some embodiments, the structural unit

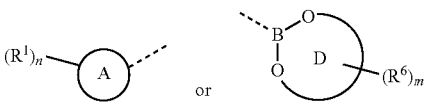

of the compound of formula (I-a) is as defined above for the compound of formula (I).

In some embodiments, the compound of formula (I-a) disclosed herein is a prodrug of a compound of formula (I-a-0),

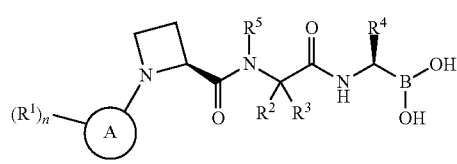
(I-a-0)

wherein ring A, n, $R^1$, $R^2$, $R^3$, $R^4$ and $R^5$ are as defined above for the compound of formula (I).

In some embodiments, the structural unit

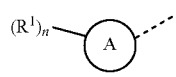

of the compound of formula (I-a-0) is as defined above for the compound of formula (I).

In another aspect, the present application also provides a compound of formula (II), or a pharmaceutically acceptable salt thereof, a tautomer thereof, a stereoisomer thereof or a geometric isomer thereof,

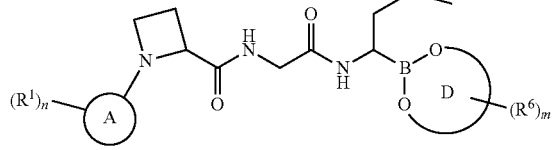
(II)

wherein ring A, ring D, n, $R^1$, $R^6$ and m are as defined above for the compound of formula (I).

In some embodiments, the structural unit

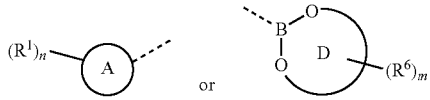

of the compound of formula (II) is as defined above for the compound of formula (I).

In another aspect, the present application also provides a compound of formula (II-a), or a pharmaceutically acceptable salt thereof, a tautomer thereof, a stereoisomer thereof or a geometric isomer thereof, (II-a)

wherein ring A, ring D, n, $R^1$, $R^6$ and m are as defined above for the compound of formula (II).

In some embodiments, the structural unit of the compound of formula (II-a) is as defined above for the compound of formula (II).

In another aspect, the present application also provides a compound of formula (III), or a pharmaceutically acceptable salt thereof, a tautomer thereof, a stereoisomer thereof or a geometric isomer thereof, (III)

wherein ring A, n, $R^6$, m and $R^1$ are as defined above for the compound of formula (I).

In some embodiments, the structural unit

of the compound of formula (III) is as defined above for the compound of formula (I).

In some embodiments, the structural unit

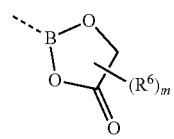

of the compound of formula (III) is selected from the group consisting of

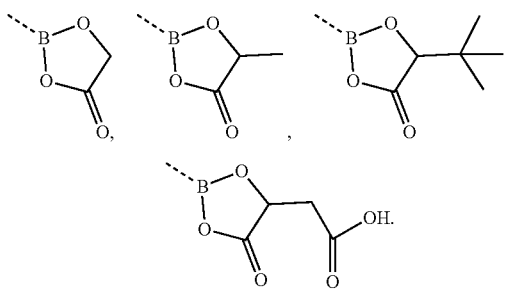 and

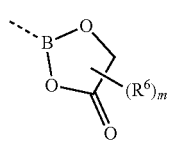

In some embodiments, the structural unit

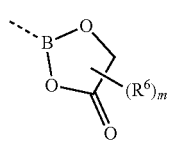

of the compound of formula (III) is

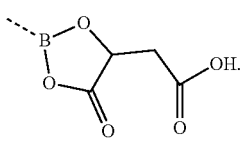

In some embodiments, the structural unit

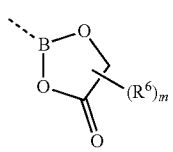

of the compound of formula (III) is selected from the group consisting of

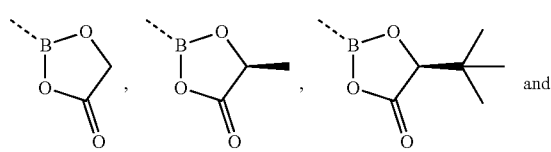 and

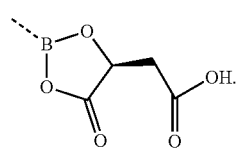

In some embodiments, the structural unit compound of formula (III) is

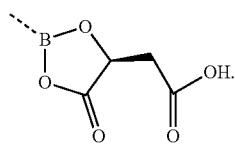

In another aspect, the present application also provides a compound of formula (III-a), or a pharmaceutically acceptable salt thereof, a tautomer thereof, a stereoisomer thereof or a geometric isomer thereof, (III-a)

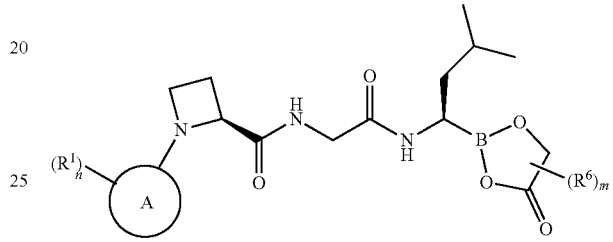

wherein ring A, n, $R^1$, $R^6$ and m as well as the structural units

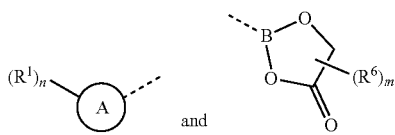

of the compound of formula (III-a) are as defined above for the compound of formula (III).

In another aspect, the present application also provides a compound of formula (IV), or a pharmaceutically acceptable salt thereof, a tautomer thereof, a stereoisomer thereof or a geometric isomer thereof, (IV)

wherein ring A, n and $R^1$ are as defined above for the compound of formula (I); X is selected from —C($R^a$)$_2$— and Y is selected from —C($R^b$)$_2$—; or X is selected from =C($R^c$)— and Y is selected from =C($R^d$)—; wherein $R^a$, $R^b$, $R^c$ and $R^d$ are each independently selected from the group consisting of hydrogen and $C_{1-6}$ alkyl, wherein the $C_{1-6}$ alkyl is optionally substituted by one or more —COOH; or $R^a$ and $R^b$ are connected to form a 3-6 membered ring; or $R^c$ and $R^d$ are connected to form a 3-6 membered ring.

In some embodiments, the structural unit

of the compound of formula (IV) is as defined above for the compound of formula (I).

In some embodiments, in the compound of formula (IV), $R^a$, $R^b$, $R^c$ and $R^d$ are each independently selected from the group consisting of hydrogen and $C_{1-6}$ alkyl, wherein the $C_{1-6}$ alkyl is optionally substituted by one or more —COOH; or $R^c$ and $R^d$ are connected to form a 3-6 membered ring.

In some embodiments, in the compound of formula (IV), $R^a$, $R^b$, $R^c$ and $R^d$ are each independently selected from the group consisting of hydrogen and $C_{1-6}$ alkyl; or $R^a$ and $R^b$ are connected to form a 3-6 membered ring; or $R^c$ and $R^d$ are connected to form a 3-6 membered ring.

In some embodiments, in the compound of formula (IV), $R^a$ and $R^b$ are each independently selected from the group consisting of hydrogen and $C_{1-6}$ alkyl; or $R^c$ and $R^d$ are connected to form a 5-6 membered ring.

In some embodiments, in the compound of formula (IV), $R^a$ and $R^b$ are each independently selected from the group consisting of hydrogen and $C_{1-3}$ alkyl; or $R^c$ and $R^d$ are connected to form phenyl.

In some embodiments, in the compound of formula (IV), $R^a$ is methyl and $R^b$ is hydrogen; or $R^c$ and $R^d$ are connected to form phenyl.

In some embodiments, the structural unit

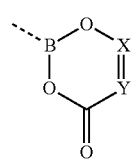

in the compound of formula (IV) is selected from the group consisting of

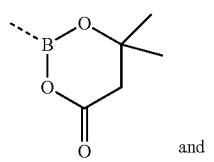 and 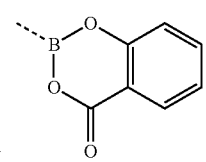.

In another aspect, the present application also provides a compound of formula (IV-a), or a pharmaceutically acceptable salt thereof, a tautomer thereof, a stereoisomer thereof or a geometric isomer thereof,

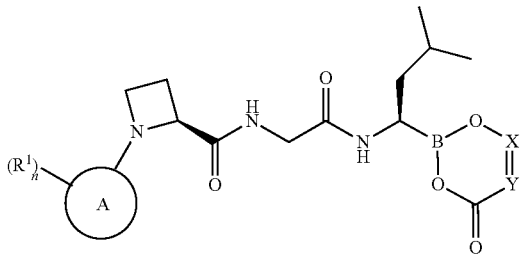

(IV-a)

wherein ring A, n, $R^1$, X and Y are as defined above for the compound of formula (IV).

In some embodiments, the structural unit

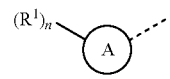

of the compound of formula (IV-a) is as defined above for the compound of formula (I).

In some embodiments, the compound of formula (II), the compound of formula (III), or the compound of formula (IV) disclosed herein is a prodrug of a compound of formula (II-0),

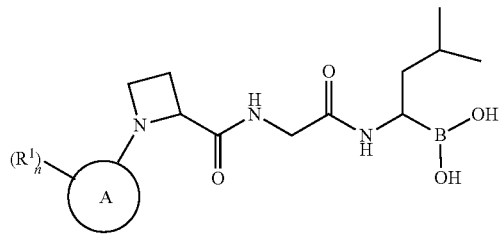

(II-0)

wherein ring A, n and $R^1$ are as defined above for the compound of formula (I).

In some embodiments, the structural unit

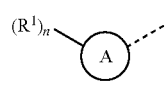

of the compound of formula (II-0) is as defined above for the compound of formula (I).

In some embodiments, the compound of formula (II-a), the compound of formula (III-a) or the compound of formula (IV-a) of the present application is a prodrug of a compound of formula (II-a-0), (II-a-0)
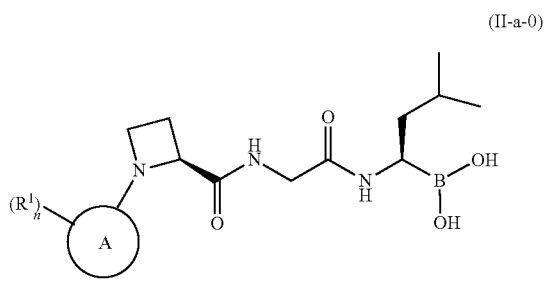
wherein ring A, n and $R^1$ are as defined above for the compound of formula (I).
In some embodiments, the structural unit
of the compound of formula (II-a-0) is as defined above for the compound of formula (I).
In another aspect, the present application also provides a compound selected from the group consisting of the following structural formulae:
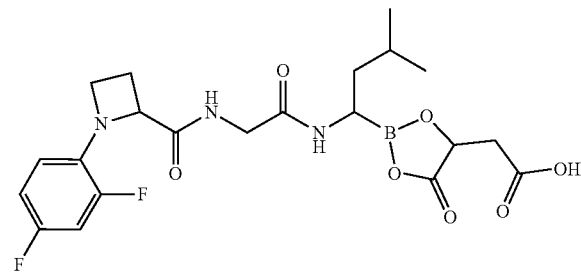
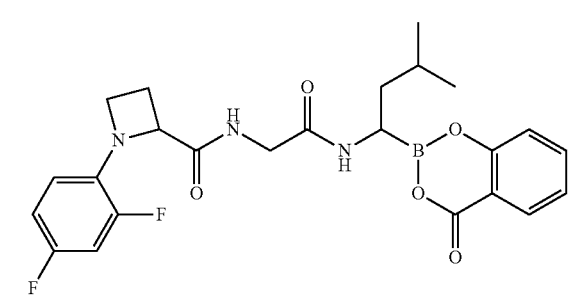
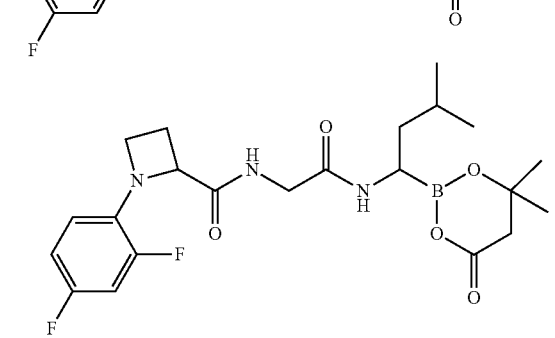
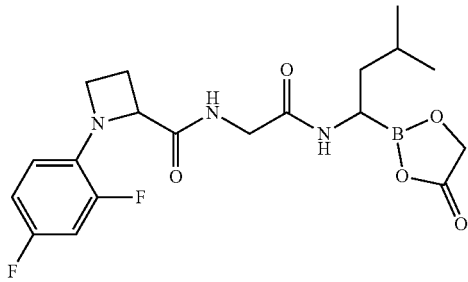
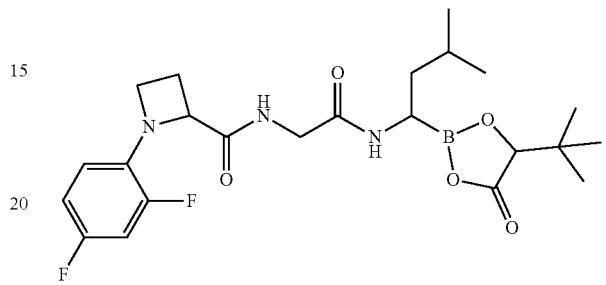
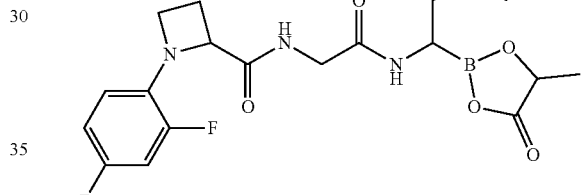
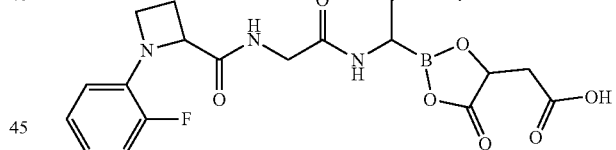
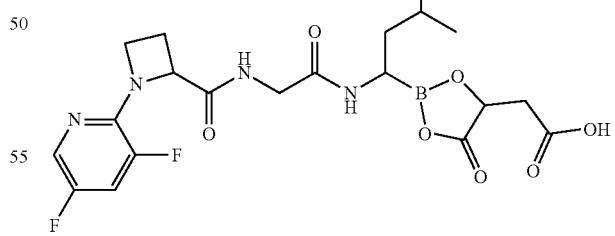
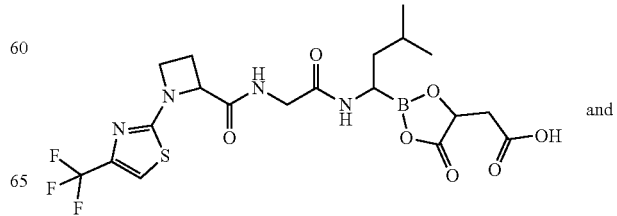
and

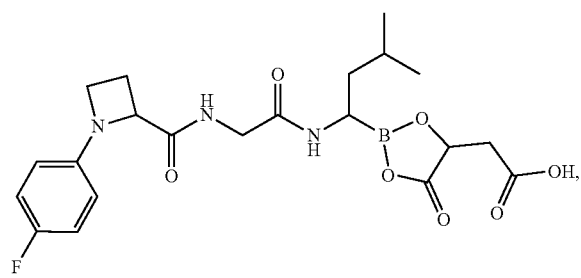

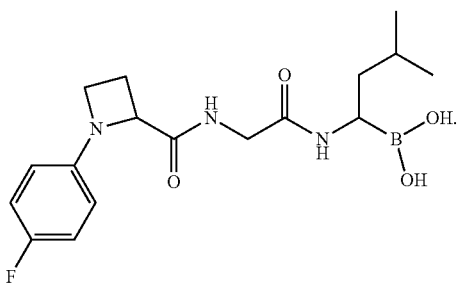

or a pharmaceutically acceptable salt thereof, a tautomer thereof, a stereoisomer thereof or a geometric isomer thereof.

In some embodiments, the above-described compounds disclosed herein are each a prodrug of the following compounds, In another aspect, the present application also provides a compound selected from the group consisting of the following structural formulae:

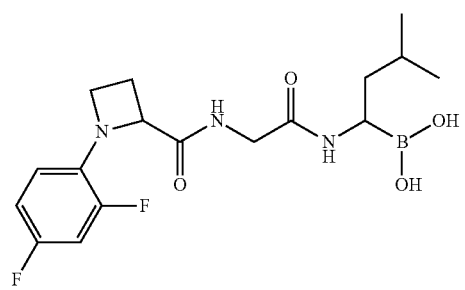

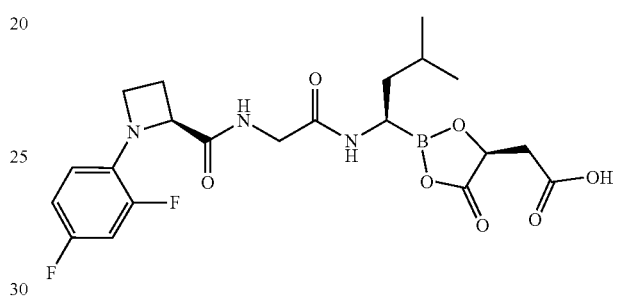

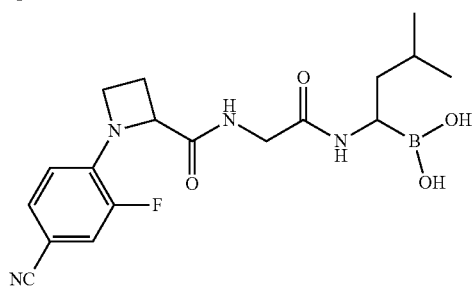

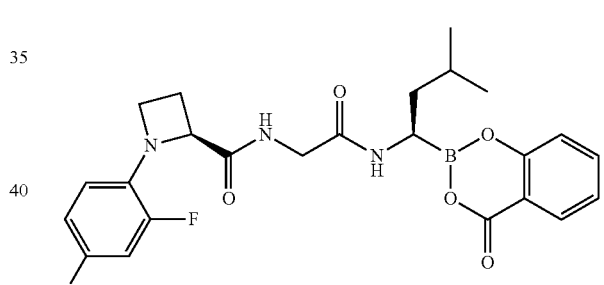

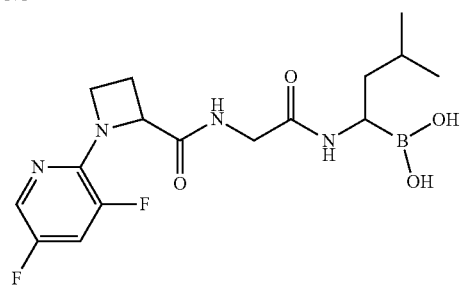

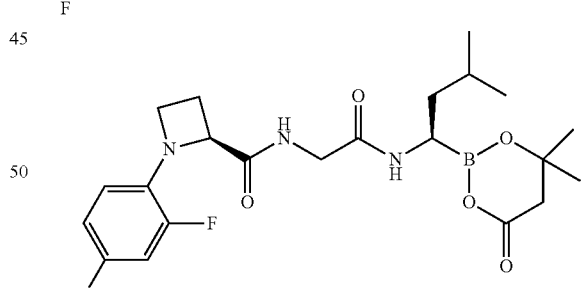

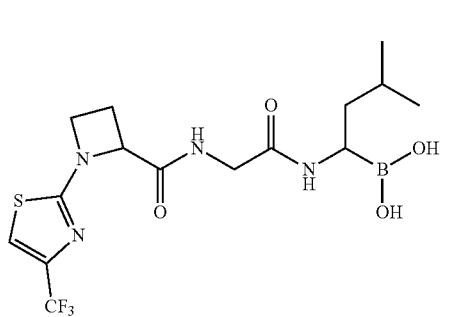

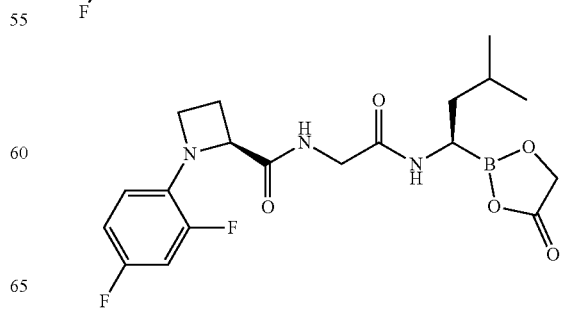

or

-continued
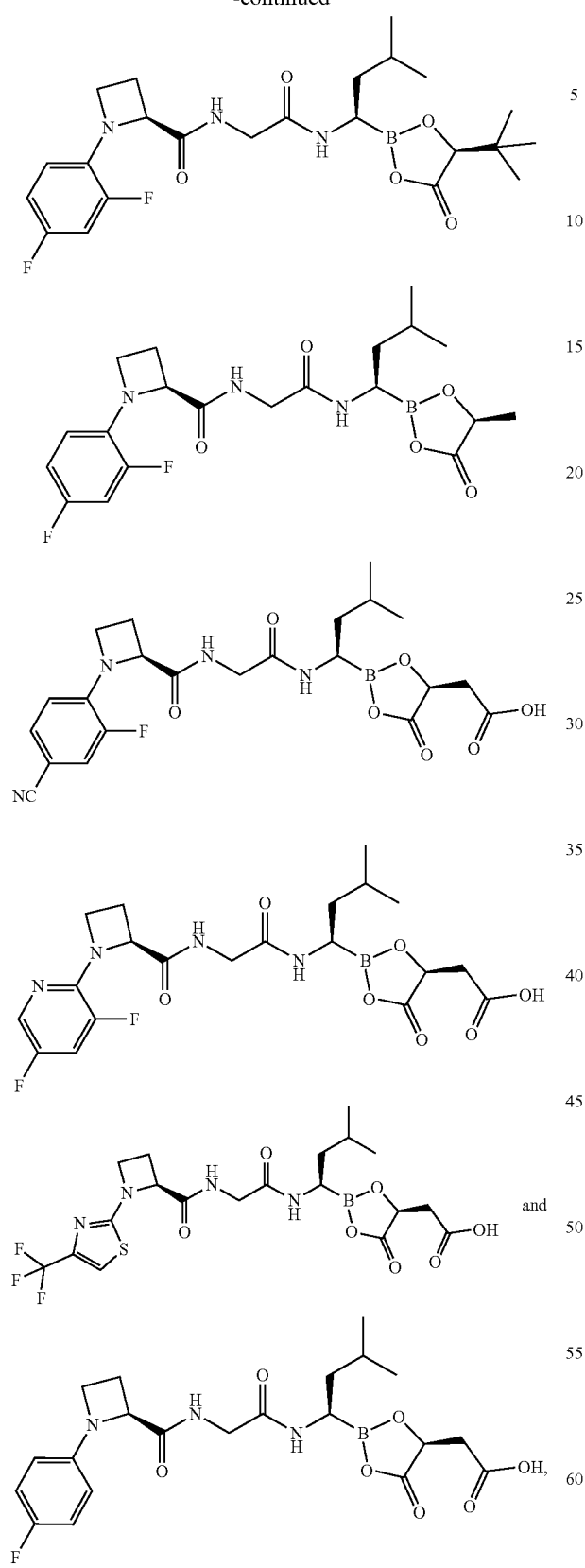
or a pharmaceutically acceptable salt thereof, a tautomer thereof or a geometric isomer thereof.
In some embodiments, the above-described compounds disclosed herein are each a prodrug of the following compounds:
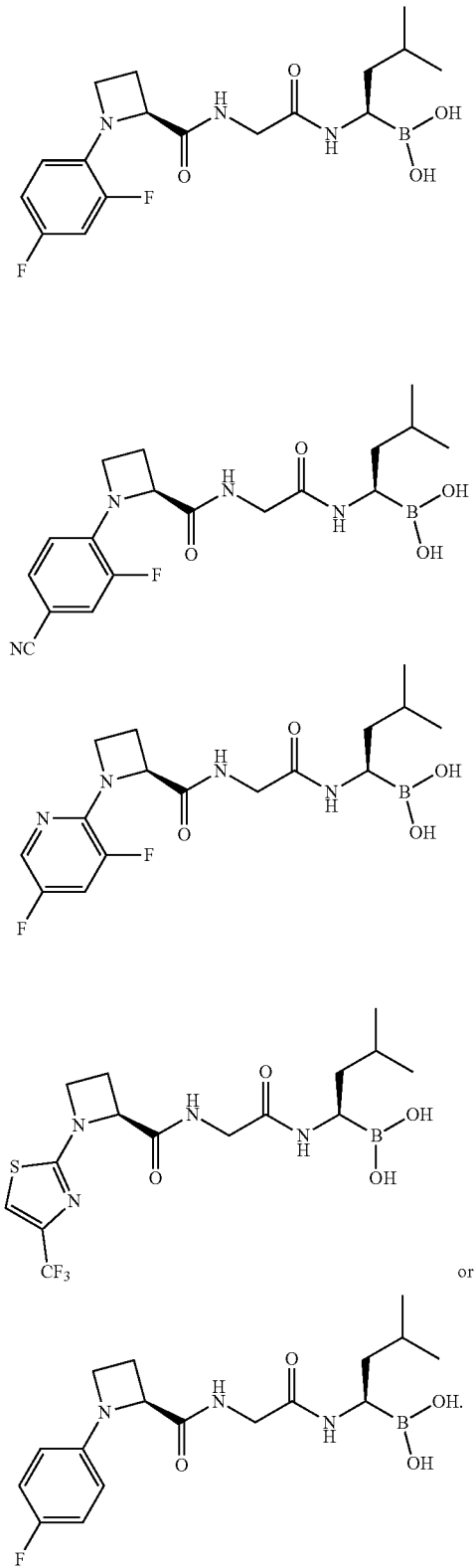
or In another aspect, the present application also provides a compound I-1:

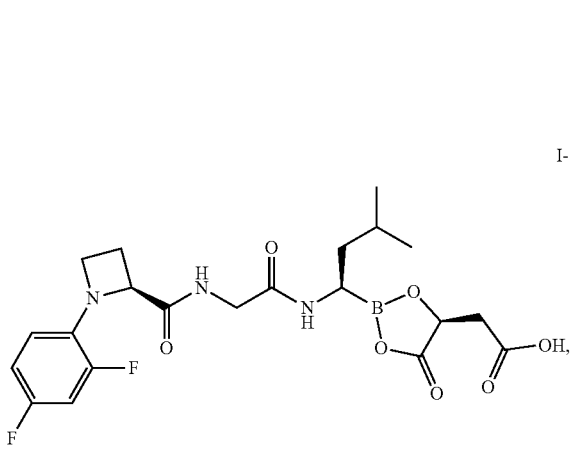 [SMILES: CC(C)C[C@H](NC(=O)CNC(=O)[C@@H]1CCN1c1ccc(F)cc1F)B1OC(=O)[C@H](CC(=O)O)O1]

or a pharmaceutically acceptable salt thereof, a tautomer thereof or a geometric isomer thereof.

In another aspect, the present application also provides a pharmaceutical composition comprising a compound of formula (I), or a pharmaceutically acceptable salt thereof, a tautomer thereof, a stereoisomer thereof or a geometric isomer thereof. In some embodiments, the pharmaceutical composition disclosed herein further comprises one or more of a pharmaceutically acceptable adjuvant, a carrier and a diluent.

In another aspect, the present application also provides a method for treating multiple myeloma in a mammal, comprising administering to a mammal, preferably a human, in need of the treatment a therapeutically effective amount of a compound of formula (I), or a pharmaceutically acceptable salt thereof, a tautomer thereof, a stereoisomer thereof or a geometric isomer thereof, or a pharmaceutical composition thereof.

In another aspect, the present application also provides use of a compound of formula (I), or a pharmaceutically acceptable salt thereof, a tautomer thereof, a stereoisomer thereof or a geometric isomer thereof, or a pharmaceutical composition thereof, in preparing a medicament for preventing or treating multiple myeloma.

In another aspect, the present application also provides use of a compound of formula (I), or a pharmaceutically acceptable salt thereof, a tautomer thereof, a stereoisomer thereof or a geometric isomer thereof, or a pharmaceutical composition thereof, in preventing or treating multiple myeloma.

In another aspect, the present application also provides a compound of formula (I), or a pharmaceutically acceptable salt thereof, a tautomer thereof, a stereoisomer thereof or a geometric isomer thereof, or a pharmaceutical composition thereof, for preventing or treating multiple myeloma.

In another aspect, the present application provides a crystal of compound I-1, which has excellent properties in at least one of pharmacokinetics, bioavailability, hygroscopicity, stability, solubility, purity, ease of preparation, and the like,

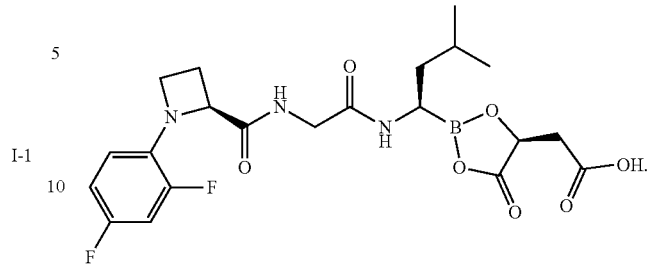

The present application provides a Form I crystal of compound I-1, characterized in that, in the X-ray powder diffraction (XRPD) pattern using Cu-Kα ray, the Form I crystal of compound I-1 has diffraction peaks at the following 2θ of about 6.00, 11.98, 17.88, 20.88 and 21.48. In some embodiments, the Form I crystal of compound I-1 has diffraction peaks at following 2θ of about 6.00, 8.90, 11.98, 17.88, 20.88, 21.48, 24.60 and 25.44. In some embodiments, the Form I crystal of compound I-1 has diffraction peaks at following 2θ of about 6.00, 8.90, 11.98, 13.70, 16.50, 17.88, 20.88, 21.48, 24.60 and 25.44. In some embodiments, the Form I crystal of compound I-1 has diffraction peaks at following 2θ of about 6.00, 8.90, 11.98, 12.80, 13.70, 16.50, 17.88, 20.88, 21.48, 24.60, 25.44, 27.66, 28.94 and 30.25.

Further, in the X-ray powder diffraction pattern of the Form I crystal of the compound I-1 disclose herein using Cu-Kα ray, the peak positions and relative intensities of diffraction peaks are as shown in Table 1 below:

TABLE 1

Peak Positions And Relative Intensities Of Diffraction Peak In The X-Ray Powder Diffraction Pattern Of Form I Crystal Of Compound I-1.

| Number | 2θ (degree) | Relative intensity (I/I₀) |
|---|---|---|
| 1 | 6.00 | 100.0 |
| 2 | 8.90 | 14.7 |
| 3 | 11.98 | 25.9 |
| 4 | 12.80 | 4.3 |
| 5 | 13.70 | 9.4 |
| 6 | 16.50 | 9.7 |
| 7 | 17.88 | 75.3 |
| 8 | 20.88 | 31.8 |
| 9 | 21.48 | 37.1 |
| 10 | 24.60 | 9.9 |
| 11 | 25.44 | 13.9 |
| 12 | 27.66 | 4.1 |
| 13 | 28.94 | 3.6 |
| 14 | 30.25 | 5.4 |

In a specific embodiment, the XRPD pattern of the Form I crystal of compound I-1 provided herein is shown in FIG. 1.

In a specific embodiment, the present application provides a Form I crystal of compound I-1, wherein the crystal is characterized by: crystal system:monoclinic system; space group: P 21; cell parameters: a=24.4220(5) Å, b=8.4507(2) Å, c=24.4590(5) Å, α=90 degrees, β=107.683(1) degrees, γ=90 degrees; Z=8.

In the present application, the instrument for X-ray powder diffraction spectrometry is Bruker D8 Advance ray diffractometer, and the conditions and methods are: X-ray tube: Cu, Kα, (λ=1.54056 Å), 40 kv 40 mA; slit: 0.60 mm/10.50 mm/7.10 mm; scan range: 3-40° or 4-40°, time [s]: 0.12; step length: 0.02°.

For any given crystal form, the relative intensities of the diffraction peaks may vary due to preferred orientations resulting from, e.g., crystal morphology, as is well known in the field of crystallography. The peak intensity may vary at a place where there is preferred orientation effect, but the diffraction peak position of the crystal form cannot. In addition, there may be slight errors in the position of the peaks for any given crystal form, as is also well known in the field of crystallography. For example, the position of the peak may shift due to temperature changes, sample movement or calibration of the instrument when analyzing a sample, and the error in the measurement of 2θ value is sometimes about ±0.2 degree, and therefore, it is well known to those skilled in the art that this error should be taken into account when determining each crystal structure.

In another aspect, the present application provides a method for preparing a Form I crystal of compound I-1, comprising the step of precipitating the compound I-1 from a solvent, wherein the solvent is selected from one or more of the group consisting of isopropyl acetate, methanol, ethanol, isopropanol, n-butanol, acetonitrile, acetone, ethyl acetate, methyl tert-butyl ether, n-heptane and 2-methyltetrahydrofuran.

In some embodiments, the solvent is isopropyl acetate.

In some embodiments, the present application provides a method for preparing a Form I crystal of compound I-1, comprising the steps of:

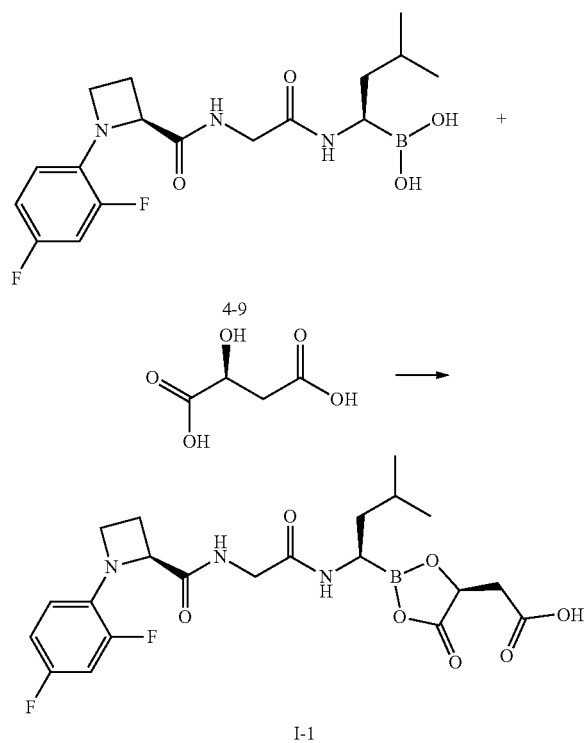

1) allowing L-malic acid to react with compound 4-9 in isopropyl acetate to give compound I-1; and
2) precipitating a solid.

In some embodiments, the step 1) is: dissolving L-malic acid in isopropyl acetate, dissolving compound 4-9 in isopropyl acetate, and mixing the two solutions.

In some embodiments, the step 2) is followed by separating the solid precipitated in step 2). In some specific embodiments, after the solid precipitated in step 2) is separated, the separated solid is dried.

In still another aspect, the present application provides a crystal composition comprising the crystal of compound I-1, wherein the crystal of compound I-1 accounts for more than 50%, preferably more than 80%, more preferably more than 90%, and most preferably more than 95% of the weight of the crystal composition, and wherein the crystal of compound I-1 is a Form I crystal of compound I-1.

In yet another aspect, the present application provides a pharmaceutical composition comprising a therapeutically effective amount of a crystal of compound I-1 described herein, or a crystal composition thereof, wherein the crystal of compound I-1 is a Form I crystal of compound I-1. The pharmaceutical composition disclosed herein may or may not contain a pharmaceutically acceptable excipient. In addition, the pharmaceutical composition disclosed herein may further comprise one or more other therapeutic agents.

In another aspect, the present application also provides a method for treating multiple myeloma in a mammal, comprising administering to a mammal, preferably a human, in need of the treatment with a therapeutically effective amount of a crystal of compound I-1 or a crystal composition thereof, or a pharmaceutical composition thereof, wherein the crystal of compound I-1 is a Form I crystal of compound I-1.

In another aspect, the present application further provides use of a crystal of compound I-1 or a crystal composition thereof, or a pharmaceutical composition thereof, in preparing a medicament for preventing or treating multiple myeloma, wherein the crystal of compound I-1 is a Form I crystal of compound I-1.

In another aspect, the present application also provides use of a crystal of compound I-1 or a crystal composition thereof, or a pharmaceutical composition thereof, in preventing or treating multiple myeloma, wherein the crystal of compound I-1 is a Form I crystal of compound I-1.

In another aspect, the present application also provides a crystal of compound I-1 or a crystal composition thereof, or a pharmaceutical composition thereof, for preventing or treating multiple myeloma, wherein the crystal of compound I-1 is a Form I crystal of compound I-1.

Definitions

Unless otherwise stated, the following terms used in the present application shall have the following meanings. A specific term, unless otherwise specifically defined, should not be considered uncertain or unclear, but construed according to its common meaning in the field. When referring to a trade name, it is intended to refer to its corresponding commercial product or its active ingredient.

The dotted line ( ---- ) in a structural unit or group in the present application represents a covalent bond.

The term "substituted" means that any one or more hydrogen atoms on a specific atom are substituted by substituents, as long as the valence of the specific atom is normal and the resulting compound is stable. When the substituent is oxo (namely =O), it means that two hydrogen atoms are substituted, and oxo is not available on an aromatic group.

The terms "optional" or "optionally" means that the subsequently described event or circumstance may, but not necessarily, occur. The description includes instances where the event or circumstance occurs and instances where it does not. For example, ethyl being optionally substituted by halogen means that the ethyl may be unsubstituted (—CH$_2$CH$_3$), monosubstituted (for example, —CH$_2$CH$_2$F), polysubstituted (for example, —CHFCH$_2$F, —CH$_2$CHF$_2$ and the like) or fully substituted (—CF$_2$CF$_3$). It will be appreciated by those skilled in the art that for any groups comprising one or more substituents, any substitutions or substituting patterns which may not exist or cannot be synthesized spatially are not introduced.

When any variable (e.g., R$^1$) occurs more than once in the constitution or structure of a compound, the definition of the variable in each case is independent. For example, if a group is substituted by 0-2 R$^1$, the group can be optionally substituted by two R$^1$ at most, and the definition of R$^1$ in each case is independent. For another example, each R$^1$ in the structural unit

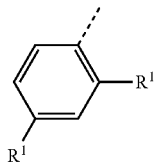

is independent, and they may be the same or different. Furthermore, a combination of a substituent and/or a variant thereof is permissible only if the combination can result in a stable compound.

C$_{m-n}$ in the present application means that the portion has an integer number of carbon atoms in the given range m-n. For example, "C$_{1-6}$" means that the group may have 1 carbon atom, 2 carbon atoms, 3 carbon atoms, 4 carbon atoms, 5 carbon atoms or 6 carbon atoms.

The term "halo-" or "halogen" refers to fluorine, chlorine, bromine and iodine.

The term "amino" refers to —NH$_2$ group.

The term "alkyl" refers to hydrocarbyl with a general formula of C$_n$H$_{2n+1}$. The alkyl can be linear or branched. For example, the term "C$_{1-6}$ alkyl" refers to alkyl with 1-6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.).

The terms "heterocyclic ring", "heterocyclyl" and "heterocyclic group" can be used interchangeably and refer to a stable 3-7 membered monocyclic or fused 7-10 membered or bridged 6-10 membered bicyclic heterocyclic moiety that is saturated or partially unsaturated and has one or more heteroatoms in addition to carbon atoms. The heteroatom can be selected from one or more of the group consisting of N, S and O. The heterocyclic ring may be attached to its pendant group at any heteroatom or carbon atom that results in a stable structure, and any of the ring atoms may be optionally substituted. Examples of the saturated or partially unsaturated heterocyclyl include, but are not limited to: tetrahydrofuranyl, tetrahydrothienyl, pyrrolidinyl, pyrrolidinonyl, piperidinyl, pyrrolinyl, tetrahydroquinolyl, tetrahydroisoquinolyl, decahydroquinolyl, oxazolidinyl, piperazinyl, dioxanyl, dioxolanyl, diazepinyl, oxoazepinyl, thiazepinyl, morpholinyl, and quinuclidinyl.

The term "cycloalkyl" refers to a fully saturated carbon ring existing in the form of a monocyclic, bridged cyclic or spiro structure. Unless otherwise specified, the carbon ring is generally a 3-10 membered ring. Non-limiting examples of cycloalkyl include, but are not limited to, cyclopropyl, cyclobutyl, cyclopentyl, cyclohexyl, norbornyl(bicyclo[2.2.1]heptyl), bicyclo[2.2.2]octyl, adamantyl and the like.

The term "aryl" refers to an aromatic monocyclic or fused polycyclic group of carbon atoms with the conjugated pi-electron system. For example, an aryl may have 6-20 carbon atoms, 6-14 carbon atoms or 6-12 carbon atoms. Non-limiting examples of aryl include, but are not limited to: phenyl, naphthyl, anthryl, 1,2,3,4-tetrahydronaphthalene, and the like.

The term "heteroaryl" refers to a monocyclic or fused polycyclic system which comprises at least one ring atom selected from the group consisting of N, O and S, with the remaining ring atoms being C, and which has at least one aromatic ring. Preferably, heteroaryl has a single 4-8 membered ring, in particular, a 5-8 membered ring, or is a plurality of fused rings comprising 6-14 ring atoms, in particular 6-10 ring atoms. Non-limiting examples of heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl and the like.

The term "heteroalkyl" is a linear or branched alkyl having preferably 1-14 carbons, more preferably 1-10 carbons, further more preferably 1-6 carbons, and most preferably 1-3 carbons in the chain, wherein one or more carbons are substituted by a heteroatom selected from the group consisting of S, O and N. Exemplary heteroalkyl includes alkyl ether, secondary alkylamine and tertiary alkylamine, alkyl amide, alkyl sulfide, and the like, such as alkoxy, alkylthio and alkylamino; unless otherwise specified, C$_{1-6}$ heteroalkyl includes C$_1$, C$_2$, C$_3$, C$_4$, C$_5$ and C$_6$ heteroalkyl, e.g., C$_{1-6}$ alkoxy, C$_{1-6}$ alkylthio, C$_{1-6}$ alkylamino.

The term "alkoxyl" refers to —O-alkyl.

The term "treating" means administering the compound or formulation described herein to prevent, ameliorate or eliminate a disease or one or more symptoms associated with the disease, and includes:
(i) preventing the occurrence of the disease or disease state in a mammal, particularly when such a mammal is predisposed to the disease state but has not yet been diagnosed as having it;
(ii) inhibiting a disease or disease state, i.e., arresting its development; and
(iii) alleviating a disease or disease state, i.e., causing its regression.

The term "therapeutically effective amount" refers to an amount of the compound disclosed herein for (i) treating or preventing a specific disease, condition or disorder; (ii) alleviating, improving or eliminating one or more symptoms of a specific disease, condition or disorder, or (iii) preventing or delaying onset of one or more symptoms of a specific disease, condition or disorder described herein. The amount of the compound disclosed herein composing the "therapeutically effective amount" varies dependently on the compound, the disease state and its severity, the administration regimen, and the age of the mammal to be treated, but can be determined routinely by those skilled in the art in accordance with their knowledge and the present disclosure.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound to an organic entity.

The term "pharmaceutically acceptable excipients" refers to those excipients which do not have a significant irritating effect on an organic entity and do not impair the biological activity and properties of the active compound. Suitable excipients are well known to those skilled in the art, for example carbohydrate, wax, water-soluble and/or water-swellable polymers, hydrophilic or hydrophobic material, gelatin, oil, solvent, water.

In the present application, the word "comprise" and variations thereof such as "comprises" or "comprising" will be understood in an open, non-exclusive sense, i.e., "including but not limited to".

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as prototropic tautomer) includes interconversion via proton transfer, such as keto-enol isomerization and imine-enamine isomerization. A specific example of a proton tautomer is an imidazole moiety where a proton can transfer between two ring nitrogens. A tautomer includes the interconversion via recombination of some bonding electrons.

Unless otherwise specified, the absolute configuration of a stereogenic center is represented by a wedged bond and a dashed bond (). Unless otherwise specified, the compounds disclosed herein include both E and Z geometric isomers when they contain olefinic double bonds or other centers of geometric asymmetry. Likewise, all tautomeric forms are included within the scope of the present application.

The compounds disclosed herein may exist in specific geometric isomeric or stereoisomeric forms. All such compounds are contemplated herein, including tautomers, cis-isomers and trans-isomers, (−)- and (+)-enantiomers, (R)- and (S)-enantiomers, diastereomers, (D)-isomers, (L)-isomers, and racemic mixtures and other mixtures thereof, such as an enantiomer or diastereomer enriched mixture, all of which are included within the scope of the present application. The substituents such as alkyl may have an additional asymmetric carbon atom. All these isomers and mixtures thereof are included within the scope of the present application.

The present application also comprises isotopically-labeled compounds which are identical to those recited herein but one or more atoms thereof are replaced by an atom having an atomic mass or mass number different from the atomic mass or mass number usually found in nature. Examples of isotopes that can be incorporated into the compounds disclosed herein include isotopes of hydrogen, carbon, nitrogen, oxygen, phosphorus, sulfur, fluorine, iodine, and chlorine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Certain isotopically-labeled compounds disclosed herein (e.g., those labeled with $^3H$ and $^{14}C$) can be used to analyze compounds and/or substrate tissue distribution. Tritiated (i.e., $^3H$) and carbon-14 (i.e., $^{14}C$) isotopes are particularly preferred for their ease of preparation and detectability. Positron emitting isotopes, such as $^{15}O$, $^{13}N$, $^{11}C$, and $^{18}F$ can be used in positron emission tomography (PET) studies to determine substrate occupancy. Isotopically-labeled compounds disclosed herein can generally be prepared by following procedures analogous to those disclosed in the schemes and/or examples below while substituting a non-isotopically labeled reagent with an isotopically-labeled reagent.

Furthermore, substitution with heavier isotopes such as deuterium (i.e., $^2H$) may provide certain therapeutic advantages (e.g., increased in vivo half-life or reduced dosage requirement) resulting from greater metabolic stability and hence may be preferred in some circumstances in which deuterium substitution may be partial or complete, wherein partial deuterium substitution refers to substitution of at least one hydrogen with at least one deuterium.

The compound disclosed herein can be asymmetrical, for example, has one or more stereoisomers. Unless otherwise specified, all stereoisomers are included in the present application, such as enantiomers and diastereomers. The compound with asymmetrical carbon atoms disclosed herein can be separated in an optically pure form or in a racemic form. The optically pure form can be separated from a racemic mixture or can be synthesized using a chiral raw material or a chiral reagent.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere, aerosol, and the like.

Typical routes of administration of a compound or a pharmaceutically acceptable salt thereof or a pharmaceutical composition thereof disclosed herein include, but are not limited to, oral, rectal, local, inhalation, parenteral, sublingual, intravaginal, intranasal, intraocular, intraperitoneal, intramuscular, subcutaneous, intravenous administration and the like.

The pharmaceutical composition disclosed herein can be manufactured by methods well known in the art, such as by conventional mixing, dissolving, granulating, dragee-making, levigating, emulsifying, lyophilizing, and the like.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragees, capsules, liquids, gels, slurries, suspensions and the like for oral administration to a patient.

A solid oral pharmaceutical composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents and the like.

The pharmaceutical compositions may also be suitable for parenteral administration, such as sterile solutions, suspensions or lyophilized products in suitable unit dosage forms.

In all of the administration methods of the compound of general formula (I) described herein, the daily dose administered is from 0.01 mg/kg to 200 mg/kg body weight, given in individual or separated doses.

The compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples disclosed herein.

The chemical reactions of the embodiments disclosed herein are carried out in a suitable solvent that must be suitable for the chemical changes in the present application and the reagents and materials required therefor. In order to acquire the compounds disclosed herein, it is sometimes necessary for one skilled in the art to modify or select a synthesis procedure or a reaction scheme based on the existing embodiments.

An important consideration in synthesis route planning in the art is the selection of suitable protecting groups for reactive functional groups (e.g., amino in the present application). For example, reference may be made to Greene's Protective Groups in Organic Synthesis (4th Ed.) Hoboken, N.J.: John Wiley & Sons, Inc. All references cited herein are incorporated by reference in their entirety.

In some embodiments, the compound of formula (I) disclosed herein may be prepared by one skilled in the art through the following general route and using methods known in the art:

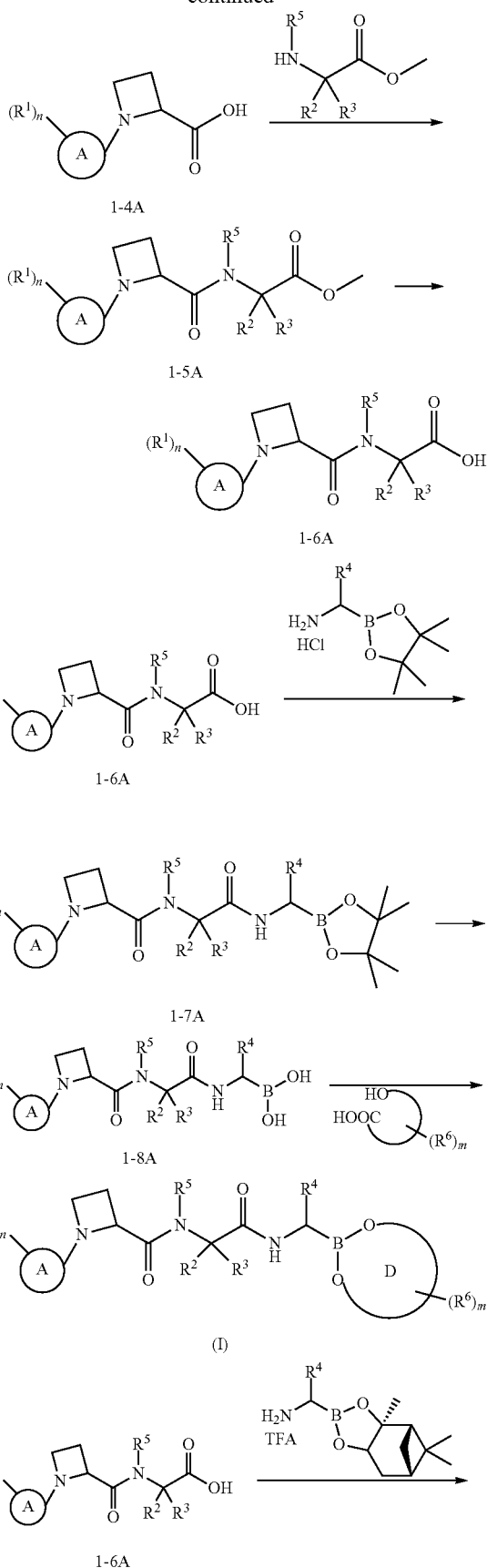

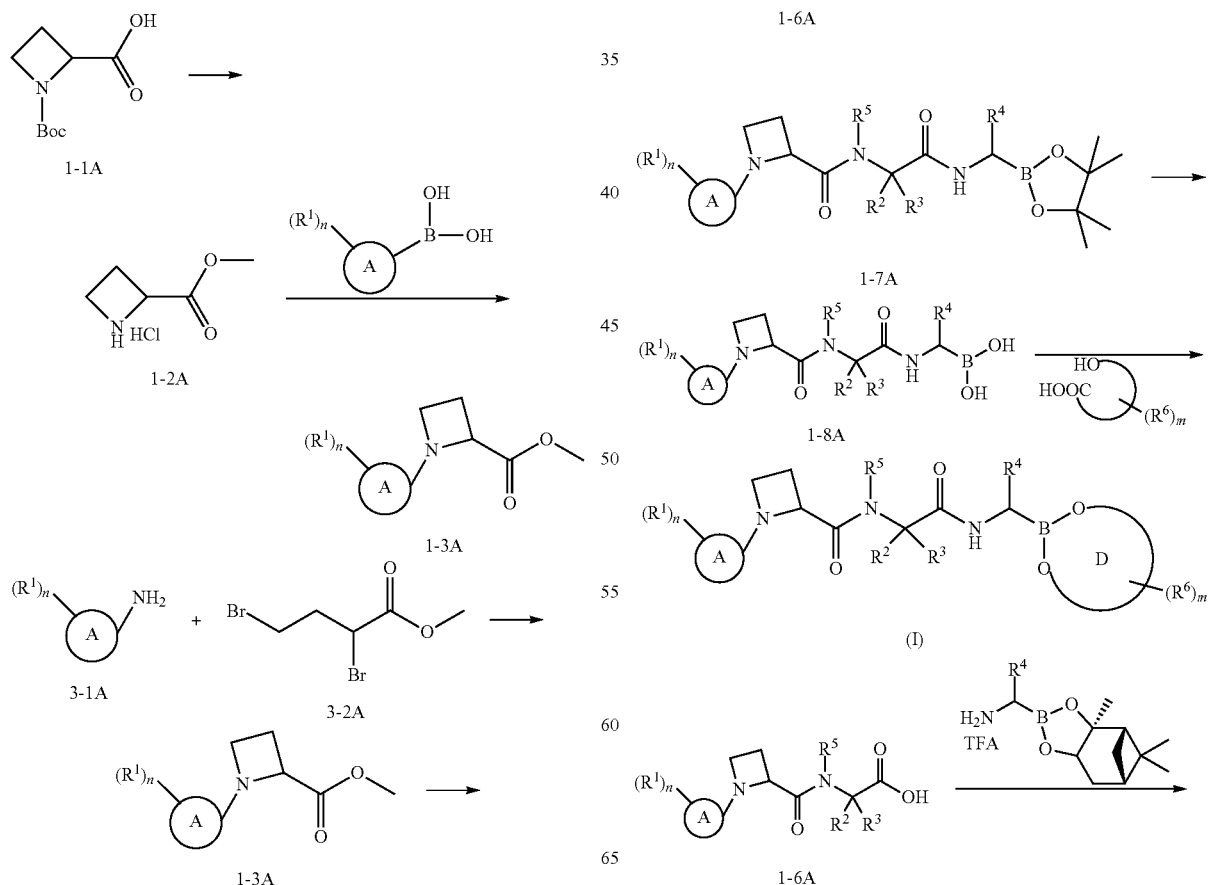

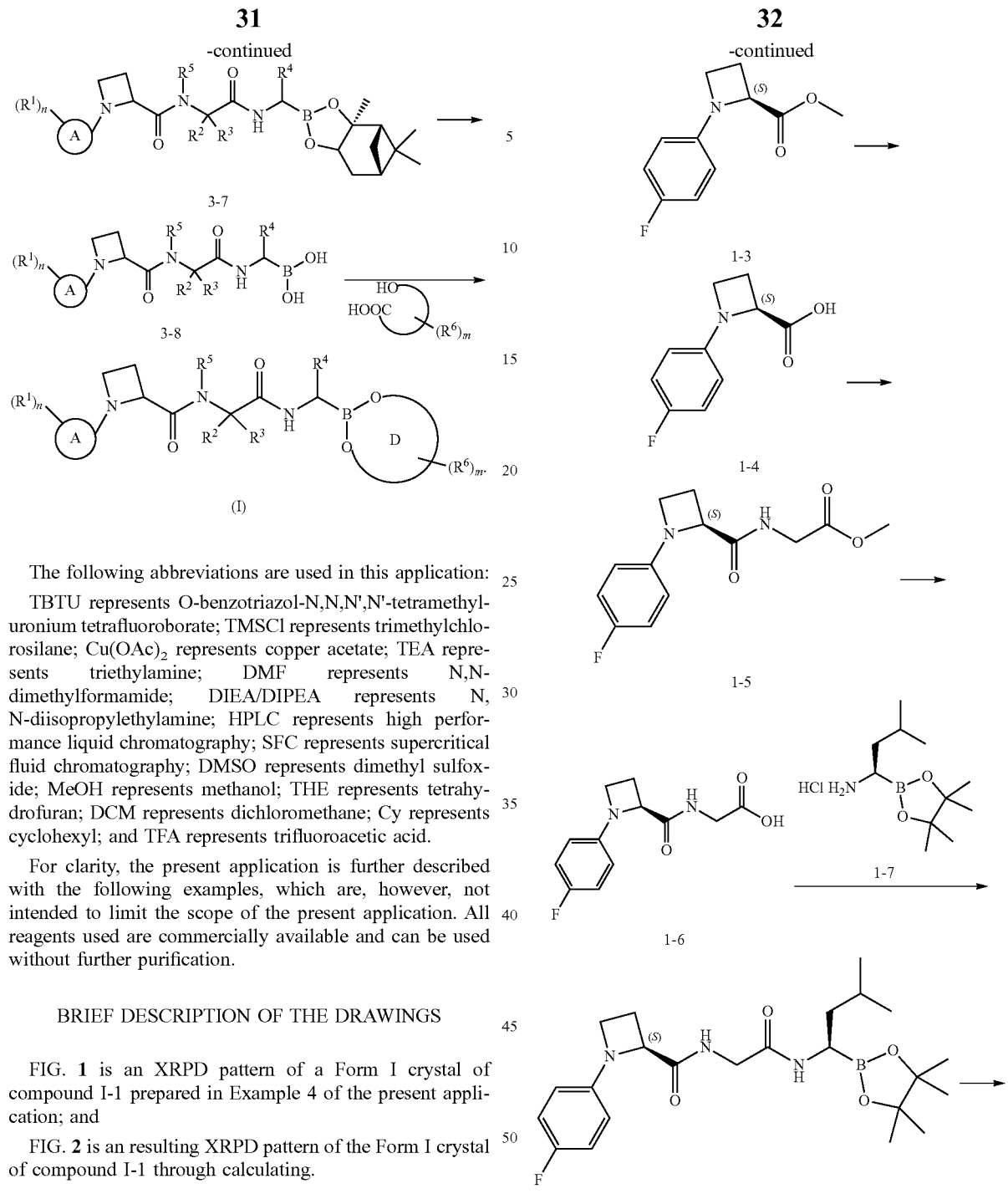

The following abbreviations are used in this application:

TBTU represents O-benzotriazol-N,N,N',N'-tetramethyluronium tetrafluoroborate; TMSCl represents trimethylchlorosilane; Cu(OAc)$_2$ represents copper acetate; TEA represents triethylamine; DMF represents N,N-dimethylformamide; DIEA/DIPEA represents N,N-diisopropylethylamine; HPLC represents high performance liquid chromatography; SFC represents supercritical fluid chromatography; DMSO represents dimethyl sulfoxide; MeOH represents methanol; THF represents tetrahydrofuran; DCM represents dichloromethane; Cy represents cyclohexyl; and TFA represents trifluoroacetic acid.

For clarity, the present application is further described with the following examples, which are, however, not intended to limit the scope of the present application. All reagents used are commercially available and can be used without further purification.

DETAILED DESCRIPTION

Example 1: Synthesis of Compound 1-9

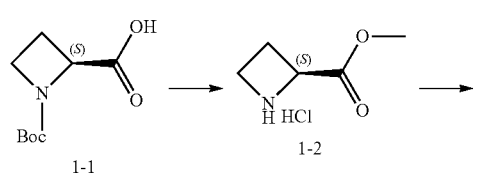

Step 1: Synthesis of Compound 1-2

Figure 1:
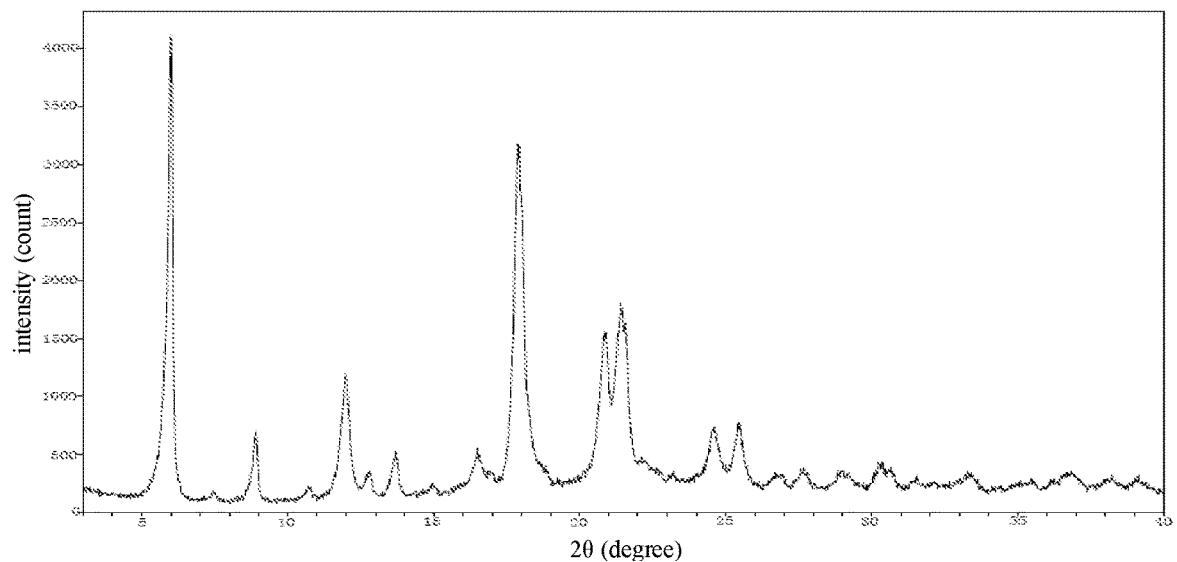
FIG. 1 is an XRPD pattern of a Form I crystal of compound I-1 prepared in Example 4 of the present application.

To a mixed solution of compound 1-1 (10.00 g) and methanol (100.00 mL) was added TMSCl (27 g) at 0° C. and the reaction mixture was stirred at room temperature for 12 hours under nitrogen atmosphere. The reaction mixture was concentrated under reduced pressure to give compound 1-2. Compound 1-2: $^1$HNMR: (400 MHz, METHANOL-$d_4$) δ 5.04-5.17 (m, 1H), 4.11 (q, J=9.12 Hz, 1H), 3.91 (dt, J=5.90, 9.98 Hz, 1H), 3.84 (s, 3H), 2.59-2.86 (m, 2H).

Step 2: Synthesis of Compound 1-3

To a solution of 4-fluorobenzeneboronic acid (7 g) in acetonitrile (80.00 mL) were added compound 1-2 (2.53 g), 4 Å molecular sieve (2.00 g), Cu(OAc)$_2$ (3.33 g) and TEA (6.75 g) at room temperature. The reaction mixture was heated to 80° C. and then stirred for 12 hours. The reaction mixture was filtered, and the filtrate was concentrated. The resulting residue was purified by silica gel column chromatography (mobile phase:petroleum ether:ethyl acetate=3:1) to give compound 1-3. Compound 1-3: $^1$HNMR: (400 MHz, CHLOROFORM-d) δ 6.87-7.02 (m, 2H), 6.41-6.54 (m, 2H), 4.45 (dd, J=7.65, 8.66 Hz, 1H), 4.00 (ddd, J=3.89, 6.71, 8.47 Hz, 1H), 3.82 (s, 3H), 3.58-3.75 (m, 1H), 2.46-2.75 (m, 2H).MS (ESI) m/z: 209.9 [M+1].

Step 3: Synthesis of Compound 1-4

To a mixed solution of compound 1-3 (700.00 mg) in methanol (3.00 mL), tetrahydrofuran (3.00 mL) and water (1.50 mL) was added LiOH·H$_2$O (702.83 mg) under an ice bath. The reaction mixture was stirred at a temperature between 0° C. and room temperature for 3 hours and then adjusted to pH=6 with 1 mol/L hydrochloric acid. The mixed solution was concentrated and extracted with ethyl acetate, and the organic phases were combined and concentrated to remove the solvent to give compound 1-4, which was used directly in the next step. Compound 1-4: MS (ESI) m/z: 195.9 [M+1].

Step 4: Synthesis of Compound 1-5

To a solution of compound 1-4 (150.00 mg) in DMF (3.00 mL) were added glycine methyl ester hydrochloride (115.78 mg), TBTU (296.09 mg) and DIEA (397.27 mg, 0.53 mL) at −10° C. The reaction mixture was stirred at −10° C.-0° C. for 3 hours, and then a saturated aqueous ammonium chloride solution (10 mL) was added. The aqueous phase was extracted with ethyl acetate. The organic phases were combined and washed with saturated brine, dried over anhydrous sodium sulfate, filtered, and concentrated to remove the solvent, and the obtained product was purified by silica gel column chromatography (mobile phase: petroleum ether:ethyl acetate=1:1) to give compound 1-5. Compound 1-5: $^1$HNMR: (400 MHz, CHLOROFORM-d) δ 7.41 (br s, 1H), 6.90-7.04 (m, 2H), 6.44-6.57 (m, 2H), 4.28-4.37 (m, 1H), 4.11 (dd, J=5.90, 8.66 Hz, 2H), 3.98 (ddd, J=3.39, 6.90, 8.53 Hz, 1H), 3.66-3.80 (m, 4H), 2.45-2.69 (m, 2H). MS (ESI) m/z: 266.9 [M+1].

Step 5: Synthesis of Compound 1-6

To a mixed solution of compound 1-5 (160.00 mg) in THF (2.00 mL), MeOH (2.00 mL), and H$_2$O (1.00 mL) was added LiOH·H$_2$O (126.07 mg). The reaction mixture was stirred at a temperature between 0° C. and room temperature for 12 hours and then adjusted to pH=3 with 1 mol/L hydrochloric acid. The mixed solution was concentrated and extracted with ethyl acetate. The organic phases were combined and concentrated to remove the solvent to give compound 1-6, which was used directly in the next step. Compound 1-6: MS (ESI) m/z: 252.9 [M+1].

Step 6: Synthesis of Compound 1-8

To a solution of compound 1-6 (150.0 mg) in DMF (5.00 mL) were added compound 1-7 (178.10 mg), TBTU (229.12 mg) and DIEA (307.42 mg, 415.43 µL) at −10° C. The reaction mixture was stirred at −10° C.-0° C. for 2 hours and then water (5 mL) was added. The aqueous phase was extracted with ethyl acetate, and the organic phases were combined and washed with saturated brine, dried over anhydrous sodium sulfate, filtered, and concentrated to remove the solvent to give compound 1-8. Compound 1-8: MS (ESI) m/z: 448.1 [M+1].

Step 7: Synthesis of Compound 1-9

To a solution of compound 1-8 (260.00 mg) in methanol (5.00 mL) were added isobutylboronic acid (414.73 mg) and aqueous HCl solution (1 mol/L, 41.55 µL) under an ice bath. The reaction mixture was warmed to room temperature and then stirred for 3 hours. The reaction mixture was concentrated under reduced pressure to give the crude product, which was purified by prep-HPLC and then separated by SFC to give compound 1-9. Compound 1-9: $^1$H NMR (400 MHz, METHANOL-$d_4$) δ 6.76-6.93 (m, 2H), 6.63 (br d, J=4.52 Hz, 2H), 4.59 (br s, 5H), 4.08 (br d, J=10.29 Hz, 1H), 2.73 (br s, 1H), 2.07-2.40 (m, 2H), 1.52-1.75 (m, 1H), 1.31 (br d, J=16.81 Hz, 2H), 0.80-0.97 (m, 6H). MS (ESI) m/z: (M-17) 347.9.

Prep-HPLC separation conditions were as follows:

Chromatographic column: Phenomenex Synergi C18 150×30 mm×4 µm;

Mobile phase: A: water (0.225% formic acid), B: methanol;

Elution gradient: B %: 55%-85%;

Appearance time: 10 min.

SFC separation conditions were as follows:

Chromatographic column: AD (250 mm×30 mm, 5 µm);

Mobile phase: A: carbon dioxide, B: methanol;

Elution gradient: B %: 20%-20%;

Flow rate: 50 mL/min;

The peak sequence is the second peak appearing in the high performance chiral liquid column chromatography.

Example 2: Synthesis of Compound 2-8

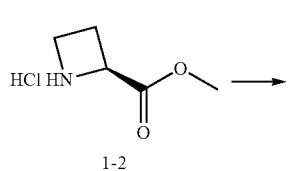

1-2

-continued

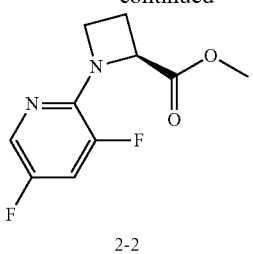

2-2

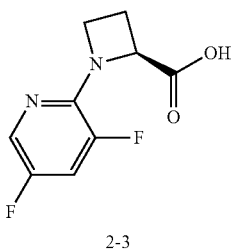

2-3

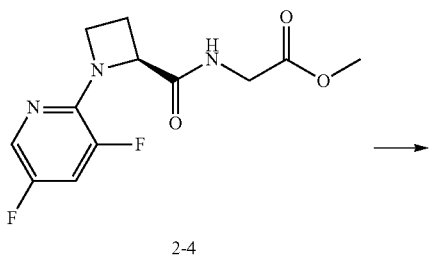

2-4

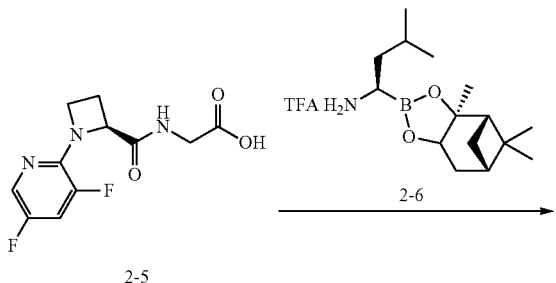

2-5

-continued

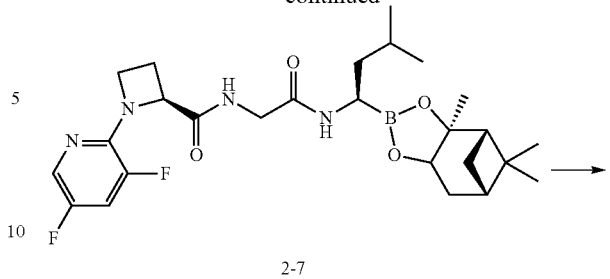

2-7

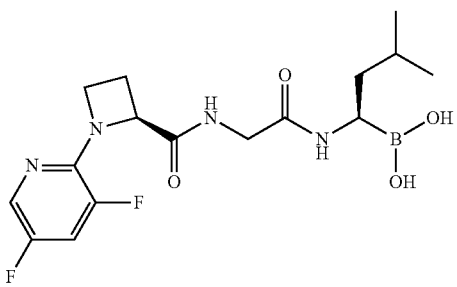

2-8

Step 1: Synthesis of Compound 2-2

To a solution of compound 1-2 (173.15 mg) and 2,3,5-trifluoropyridine (0.1 g) in DMSO (10 mL) was added $K_3PO_4$ (319.03 mg) at room temperature. The reaction mixture was heated to 120° C. and stirred for 48 hours. Then the reaction solution was transferred, diluted with water (10 mL), and extracted with ethyl acetate, and the organic phases were combined and washed with saturated brine, dried over anhydrous sodium sulfate, filtered, and concentrated to remove the solvent. The residue was separated by silica gel column chromatography (mobile phase: petroleum ether: ethyl acetate=5:1) to give compound 2-2. Compound 2-2: $^1$H NMR (400 MHz, CHLOROFORM-d) δ 7.87 (d, J=2.26 Hz, 1H), 7.06 (ddd, J=2.38, 8.09, 10.85 Hz, 1H), 4.83-4.93 (m, 1H), 4.20-4.31 (m, 1H), 3.98-4.09 (m, 1H), 3.74-3.84 (m, 3H), 2.67 (dtd, J=5.14, 8.94, 11.11 Hz, 1H), 2.49 (tdd, J=6.68, 8.78, 11.23 Hz, 1H). MS (ESI) m/z: 228.9 [M+1].

Step 2: Synthesis of Compound 2-3

To a mixed solution of compound 2-2 (280.00 mg) in MeOH (1.00 mL), THF (1.00 mL), and $H_2O$ (0.50 mL) was added $LiOH \cdot H_2O$ (257.43 mg) at 0° C. The reaction mixture was stirred at room temperature for 1 hour, and then the pH was adjusted to 6-7 with 1 mol/L hydrochloric acid, and the mixture was concentrated to give compound 2-3, which was used directly in the next step. Compound 2-3: MS (ESI) m/z: 214.9 [M+1].

Step 3: Synthesis of Compound 2-4

To a solution of compound 2-3 (0.3 g) in DCM (10 mL) were added glycine methyl ester hydrochloride (211.05 mg), TBTU (539.71 mg) and DIPEA (724.14 mg) at −10° C. The reaction mixture was stirred at −10° C.-0° C. for 3 hours, and then water (10 mL) was added. The aqueous phase was extracted with dichloromethane, and the organic phases were combined and washed with saturated brine, dried over anhydrous sodium sulfate, filtered, and concentrated to remove the solvent, and the resulting product was purified by silica gel column chromatography (mobile phase: petroleum ether:ethyl acetate=1:1) to give compound 2-4. Compound 2-4: $^1$H NMR (400 MHz, CHLOROFORM-d) δ 8.03 (s, 1H), 7.92 (d, J=2.26 Hz, 1H), 7.13 (ddd, J=2.38, 7.91, 10.79 Hz, 1H), 4.85 (t, J=8.66 Hz, 1H), 4.18 (br d, J=5.77 Hz, 1H), 4.00-4.06 (m, 1H), 3.76 (s, 3H), 2.66-2.78 (m, 1H), 2.49-2.63 (m, 1H). MS (ESI) m/z: 285.9 [M+1].

Step 4: Synthesis of Compound 2-5

To a mixed solution of compound 2-4 (0.45 g) in THF (2.00 mL), water (1.00 mL) and MeOH (2.00 mL) was added LiOH·H$_2$O (330.98 mg) at 0° C., and the reaction mixture was stirred at room temperature for 2 hours and then adjusted to pH=6 or so with 1 mol/L diluted hydrochloric acid. The mixed solution was concentrated and extracted with ethyl acetate. The organic phases were combined and concentrated to remove the solvent to give compound 2-5, which was used directly in the next step. Compound 2-5: MS (ESI) m/z: 271.9 [M+1].

Step 5: Synthesis of Compound 2-7

To a solution of compound 2-5 (0.3 g) in DCM (4.00 mL) were added compound 2-6 (503.35 mg), TBTU (426.18 mg) and DIPEA (314.50 mg, 423.85 μL) at −10° C. The reaction mixture was stirred at −10° C.-20° C. for 2 hours, and then water (10 mL) was added. The aqueous phase was extracted with dichloromethane, and the organic phases were combined and washed with saturated brine, dried over anhydrous sodium sulfate, filtered, and concentrated to remove the solvent to give compound 2-7. Compound 2-7: MS (ESI) m/z: 519.1 [M+1].

Step 6: Synthesis of Compound 2-8

To a solution of compound 2-7 (0.45 g) in MeOH (3.00 mL) were added n-hexane (4.00 mL), isobutylboronic acid (619.42 mg) and aqueous HCl solution (1 mol/L, 1.74 mL) at 0° C. The reaction mixture was stirred at 0° C.-25° C. for 12 hours, and then the reaction solution was subjected to liquid separation, and the methanol layer was adjusted to pH=5-6 with 1 mol/L NaHCO$_3$ solution. Then separation by prep-HPLC was performed to give compound 2-8. Compound 2-8: $^1$H NMR: (400 MHz, METHANOL-d$_4$) δ 7.89 (br s, 1H), 7.43 (br t, J=9.54 Hz, 1H), 4.78-4.83 (m, 1H), 3.96-4.24 (m, 4H), 2.74 (br s, 1H), 2.63 (br d, J=7.03 Hz, 1H), 2.46-2.58 (m, 1H), 1.65 (br d, J=6.02 Hz, 1H), 1.35 (br t, J=6.90 Hz, 2H), 0.92 (br d, J=5.77 Hz, 6H). MS (ESI) m/z: 367.1 [M-17].

HPLC separation conditions for Compound 2-8:
Chromatographic column: Xtimate C18 150×25 mm×5 μm
Mobile phase: A: water (containing 0.225% FA), B: methanol
Elution gradient: B %: 55%-85%
In high performance liquid column chromatography, retention time is 9.5 min.

Compound 2-9 was synthesized by the same method as in Example 2, except that compound a was used instead of 2,3,5-trifluoropyridine in step 1 of Example 2; the nuclear magnetic resonance (NMR), mass spectrometry (MS) data and HPLC separation conditions for compound 2-9 are shown in Table 2 below:

TABLE 2

| Compound number | Compound a | Structure of compound | MS-17 | $^1$HNMR | Separation conditions |
|---|---|---|---|---|---|
| 2-9 | 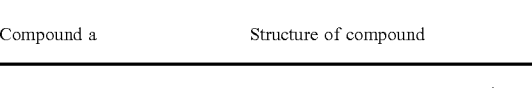 | | 405.1 | $^1$H NMR (400 MHz, METHANOL-d4) δ 7.43 (s, 1H), 4.84 (br s, 1H), 4.00-4.27 (m, 4H), 2.47-2.91 (m, 3H), 1.69 (td, J = 6.62, 13.11 Hz, 1H), 1.28-1.47 (m, 2H), 0.94 (br d, J = 6.27 Hz, 6H). | Separating by prep-HPLC; chromatographic column: Phenomenex Synergi C18 150 × 30 mm × 4 μm; mobile phase: A: water (0.225% formic acid), B: methanol (50%-75%); and the retention time in high performance liquid column chromatography is 9.4 min. |

Example 3: Synthesis of Compound 3-7

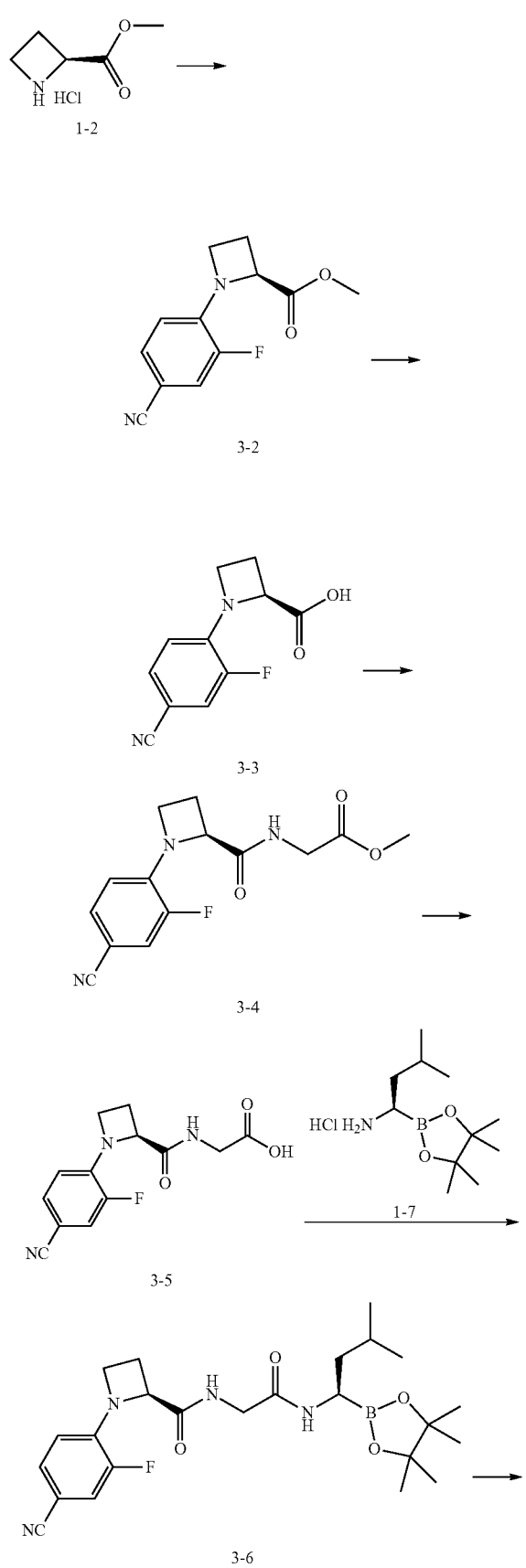

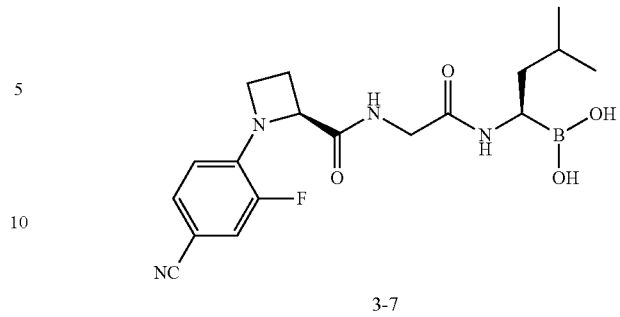

The preparation procedure of step 1 to step 4 in Example 2 was referred to so as to give compound 3-5.

Step 1: Synthesis of Compound 3-6

To a solution of compound 3-5 (300.0 mg) in DMF (5.00 mL) were added compound 1-7 (324.08 mg), TBTU (416.91 mg) and DIEA (559.39 mg, 753.90 μL) at −10° C. The reaction mixture was stirred at −10° C.-0° C. for 0.5 hour and then water (5 mL) was added. The aqueous phase was extracted with ethyl acetate, and the organic phases were combined and washed with saturated brine, dried over anhydrous sodium sulfate, filtered, and concentrated to remove the solvent to give compound 3-6. Compound 3-6: MS (ESI) m/z: 473.0 [M+1].

Step 2: Synthesis of Compound 3-7

To a solution of compound 3-6 (500.00 mg) in methanol (5.00 mL), isobutylboronic acid (755.34 mg) and aqueous HCl solution (1 mol/L, 2.12 mL) were added under an ice bath. The reaction mixture was heated to room temperature and then stirred for 3 hours. The reaction mixture was concentrated under reduced pressure and then purified by prep-HPLC, followed by SFC separation to give compound 3-7. Compound 3-7: $^1$H NMR (400 MHz, METHANOL-$d_4$) δ 7.28-7.44 (m, 2H), 6.64 (t, J=8.78 Hz, 1H), 4.73-4.80 (m, 2H), 3.96-4.32 (m, 4H), 2.62-2.81 (m, 2H), 2.38-2.57 (m, 1H), 1.64 (qd, J=6.86, 13.55 Hz, 1H), 1.23-1.43 (m, 2H), 0.93 (d, J=6.53 Hz, 6H). MS (ESI) m/z: (M-17) 373.0.

Prep-HPLC separation conditions were as follows:

Chromatographic column: Xtimate C18 150×25 mm×5 um;

Mobile phase: A: water (0.225% formic acid), B: acetonitrile;

Elution gradient: B %: 46%-76%;

Appearance time: 13 min.

SFC separation conditions were as follows:

Chromatographic column: AD (250 mm×30 mm, 5 μm);

Mobile phase: A: carbon dioxide, B: ethanol;

Elution gradient: B %: 15%-15%;

Flow rate: 50 mL/min;

The peak sequence is the second peak appearing in the high performance chiral liquid column chromatography.

Example 4: Synthesis of Compound I-1

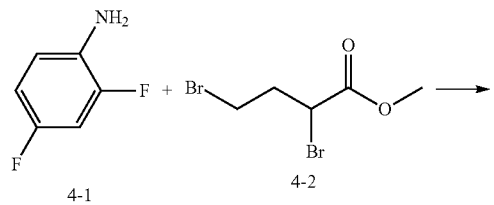

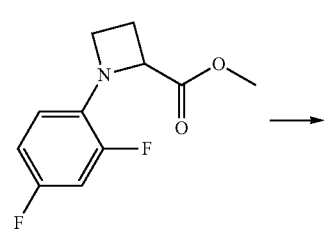

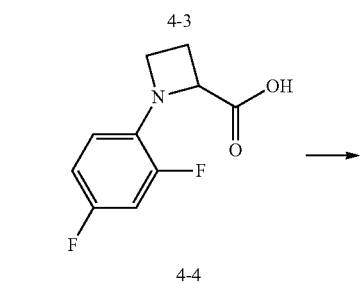

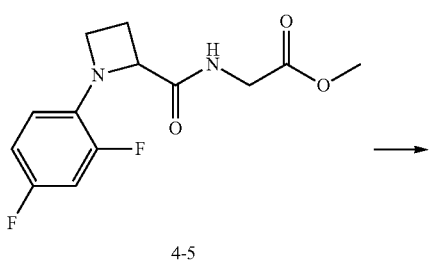

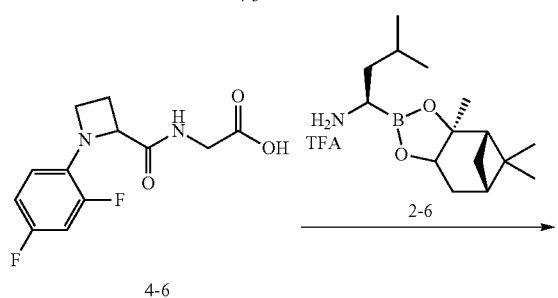

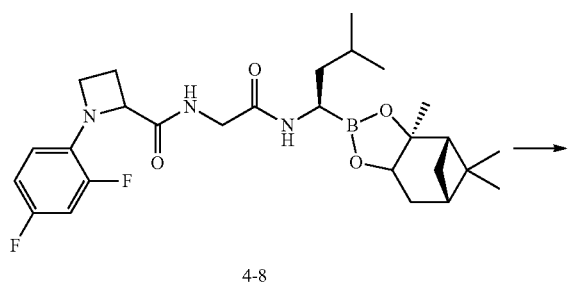

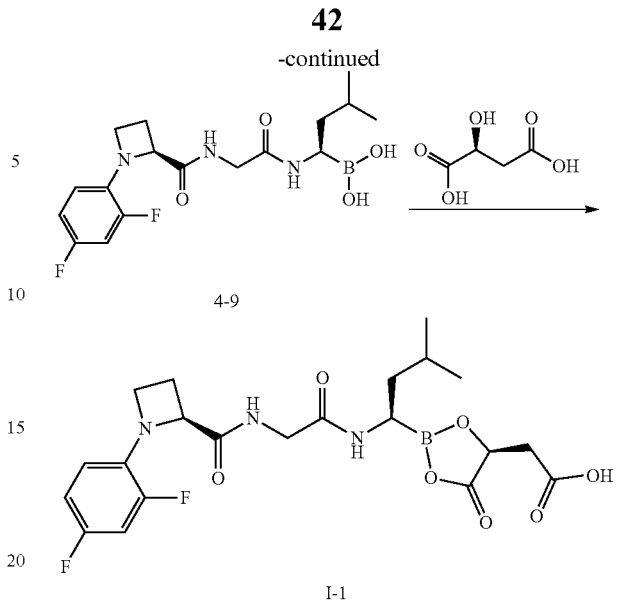

Step 1: Synthesis of Compound 4-3

N,N-diisopropylethylamine (22.02 g) was added to an acetonitrile (200 mL) solution containing compound 4-1 (10 g) and compound 4-2 (20.13 g) at room temperature. The reaction mixture was stirred at 100° C. for 16 hours, then cooled to room temperature, and then added to ethyl acetate. The organic phase was washed with water and saturated brine, and then the organic phase was dried over anhydrous sodium sulfate and filtered. The filtrate was concentrated to remove the solvent, and the residue was purified by silica gel column chromatography (mobile phase: petroleum ether:ethyl acetate=10:1) to give compound 4-3. Compound 4-3: MS (ESI) m/z: 227.9 [M+1].

Step 2: Synthesis of Compound 4-4

To a mixed solution of compound 4-3 (7.2 g) in methanol (20 mL), tetrahydrofuran (20 mL) and water (10 mL) was added LiOH·H$_2$O (6.65 g) at 0° C. The reaction mixture was stirred at room temperature for 1 hour, then concentrated under reduced pressure, diluted with water and ethyl acetate, and then subjected to liquid separation. The aqueous phase was adjusted to pH=6 with 1 mol/L hydrochloric acid, and then extracted with ethyl acetate. The organic phases were combined and washed with saturated brine, dried over anhydrous sodium sulfate and filtered. The filtrate was concentrated to remove the solvent to give compound 4-4, which was used directly in the next step. Compound 4-4: MS (ESI) m/z: 213.9 [M+1].

Step 3: Synthesis of Compound 4-5

To a solution of compound 4-4 (1.5 g) in dichloromethane (50 mL) were added glycine methyl ester hydrochloride (1.06 g), TBTU (2.71 g) and N,N-diisopropylethylamine (3.64 g) at −10° C. The reaction mixture was stirred at −10° C.-0° C. for 3 hours, then diluted with water (40 mL) and extracted with dichloromethane. The organic phases were combined, washed with saturated brine, dried over anhydrous sodium sulfate and filtered. The filtrate was concentrated to remove the solvent, and the residue was purified by silica gel column chromatography (mobile phase: petroleum ether:ethyl acetate=5:1) to give compound 4-5. Compound 4-5: MS (ESI) m/z: 284.9 [M+1].

Step 4: Synthesis of Compound 4-6

To a mixed solution of compound 4-5 (0.5 g) in tetrahydrofuran (2 mL), methanol (2 mL) and water (1 mL) was added LiOH·H$_2$O (369.03 mg) at 0° C. The reaction mixture was stirred at 0° C.-20° C. for 2 hours, then concentrated and diluted with water (3 mL), and then subjected to liquid separation. The aqueous phase was adjusted to pH=6 with 1 mol/L hydrochloric acid and extracted with ethyl acetate. The organic phases were combined, washed with saturated brine, dried over anhydrous sodium sulfate and filtered. The filtrate was concentrated to remove the solvent to give compound 4-6, which was used directly in the next reaction. Compound 4-6: MS (ESI) m/z: 270.9 [M+1].

Step 5: Synthesis of Compound 4-8

To a solution of compound 4-6 (0.26 g), compound 2-6 (437.84 mg) and TBTU (370.71 mg) in dichloromethane (10 mL) was added N,N-diisopropylethylamine (273.56 mg) at −10° C. The reaction mixture was slowly heated to room temperature and stirred for an additional 2 hours, and then the reaction mixture was diluted in water (10 mL) and extracted with dichloromethane. The organic phases were combined, washed with saturated brine, dried over anhydrous sodium sulfate and filtered. The filtrate was concentrated to remove the solvent, and the residue was purified by silica gel column chromatography (mobile phase: petroleum ether:ethyl acetate=1:1) to give compound 4-8. Compound 4-8: MS (ESI) m/z: 518.2 [M+1].

Step 6: Synthesis of Compound 4-9

To a mixed solution of compound 4-8 (0.17 g) in methanol (4 mL) and n-hexane (6 mL) were added isobutylboronic acid (234.45 mg) and 1 mol/L HCl (1.31 mL) at 0° C. The reaction mixture was slowly heated to room temperature and stirred for an additional 12 hours, and then concentrated under reduced pressure to remove the solvent to give residue. The residue was purified by prep-HPLC and then separated by SFC to give compound 4-9. Compound 4-9: $^1$H NMR (400 MHz, METHANOL-d$_4$) δ 6.83 (br s, 2H), 6.61 (br s, 1H), 4.49 (br s, 1H), 4.10 (br s, 3H), 3.84 (br s, 1H), 2.75 (br s, 1H), 2.59 (br s, 1H), 2.48 (br s, 1H), 1.62 (br s, 1H), 1.30 (br s, 2H), 0.92 (br s, 6H). MS (ESI) m/z: 366.1 [M−17].

Prep-HPLC separation method for compound 4-9:
Chromatographic column: Xtimate C18 150×25 mm, 5 m;
Mobile phase: water (0.225% FA)-MeOH;
Elution gradient: 61%-85%;
Retention time: 9.5 min.
Preparative SFC separation method for compound 4-9:
Chromatographic column: C2 250 mm×30 mm, 10 μm;
Mobile phase: A: carbon dioxide, B: methanol;
Elution gradient B %: 30%-30%;
Flow rate: 60 mL/min.

The peak sequence of the compound 4-9 is the second peak appearing in the high performance chiral liquid column chromatography.

Step 7: Synthesis of Compound I-1

Method 1: the L-malic acid (332 mg) was added to isopropyl acetate (2.5 mL), and the mixture was heated to 70° C. with stirring, and then a solution of compound 4-9 (1.0 g) in 2.5 mL of isopropyl acetate was added 10 minutes later. The heating was then stopped, and the mixture was cooled to 25° C. and stirred for an additional 5 days at this temperature. The mixed solution was filtered to collect filter cake, which was dried in vacuum to give compound I-1 which is Form I crystal of compound I-1.

Method 2: compound I-1 (68.9 g) was added to the reaction flask, and then 440 mL of isopropyl acetate was added, and the mixed solution was stirred at room temperature under nitrogen atmosphere for 24 hours. The mixed solution was filtered and dried to give Form I crystal (64.4 g) of the compound I-1 and the X-ray powder diffraction pattern of the resulting crystal using Cu-Kα ray is shown in FIG. 1.

Compound I-1: $^1$H NMR (400 MHz, DMSO-d$_6$) δ 12.30 (br s, 1H), 10.65 (br s, 1H), 8.57 (br t, J=5.77 Hz, 1H), 7.11 (ddd, J=2.64, 9.16, 12.30 Hz, 1H), 6.91 (br t, J=8.16 Hz, 1H), 6.53 (dt, J=5.65, 9.60 Hz, 1H), 4.44 (br t, J=7.91 Hz, 1H), 4.37 (dd, J=3.89, 7.65 Hz, 1H), 4.10 (br s, 2H), 3.91-4.01 (m, 1H), 3.76 (q, J=7.36 Hz, 1H), 2.61 (br d, J=10.79 Hz, 2H), 2.19-2.44 (m, 3H), 1.61 (td, J=6.71, 13.68 Hz, 1H), 1.20-1.36 (m, 2H), 0.86 (t, J=6.02 Hz, 6H).

Preparation method for a single crystal of Form I crystal of the compound I-1: 50 mg of compound I-1 was added into a microwave tube, 1 mL of ethanol was added for dissolving, and then the microwave tube was placed into a beaker filled with n-hexane for standing, and single crystals were slowly precipitated from the ethanol.

Figure 2:
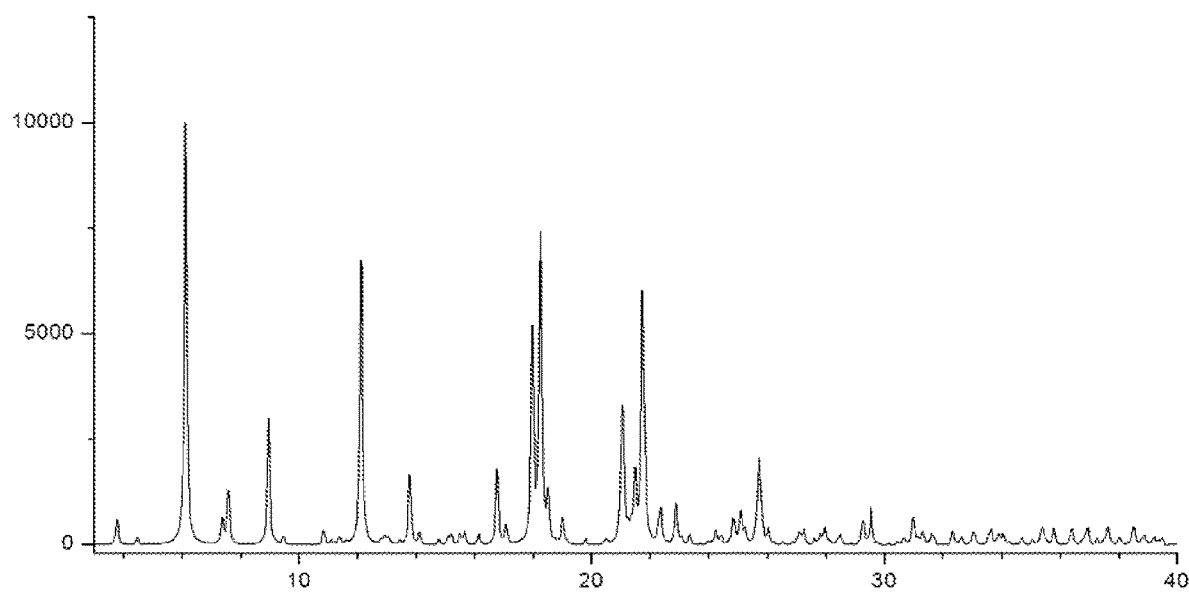
FIG. 2 is an resulting XRPD pattern of the Form I crystal of compound I-1 through calculating.

The cell parameters, crystallographic data and atomic coordinate, etc. of a single crystal of the Form I crystal of the compound I-1 are shown in Table 3 and Table 4 below, and the resulting X-ray powder diffraction pattern of the Form I crystal of the compound I-1 through calculating is shown in FIG. 2.

TABLE 3

CRYSTALLOGRAPHIC DATA AND STRUCTURE REFINEMENT

| | |
|---|---|
| Experimental molecular formula | C$_{21}$H$_{26}$BF$_2$N$_3$O$_7$ |
| Molecular weight | 481.26 |
| Temperature | 173(2) K |
| Wavelength | 1.54178 Å |
| Crystal system | Monoclinic system |
| Space group | P 21 |
| Cell parameters | a = 24.4220(5) Å |
| | b = 8.4507(2) Å |
| | c = 24.4590(5) Å |
| | α = 90 degrees |
| | β = 107.683(1) degrees |
| | γ = 90 degrees |
| Volume of crystal cell | 4809.41(18) Å$^3$ |
| Z | 8 |
| Calculating density | 1.329 Mg/m$^3$ |
| Absorption correction parameter | 0.930 mm$^{-1}$ |
| F(000) | 2016 |
| Size of crystal | 0.14 × 0.10 × 0.06 mm |
| Angle range for data collection | 1.90 to 66.66 degrees |
| Collection range for hkl | −29 <= h <= 29, −10 <= k <= 10, −29 <= l <= 28 |
| Reflection data collection/independence | 50366/16857 [R(int) = 0.0591] |
| Data integrity for theta = 66.66 | 99.7% |
| Absorption correction | From equivalent semi-experience |
| Maximum and minimum transmission | 0.3182 and 0.2066 |
| Refinement method | F2 full matrix least square method |
| Number of data/number of usage restrictions/number of parameters | 16857/1/1258 |
| Degree of fitting of F$_2$ | 2.845 |
| Final R index [I > 2sigma(I)] | R1 = 0.1429, wR2 = 0.3862 |
| R index (all data) | R1 = 0.1505, wR2 = 0.3909 |

TABLE 3-continued

CRYSTALLOGRAPHIC DATA AND STRUCTURE REFINEMENT

| | |
|---|---|
| Absolute configuration parameter | 0.2(3) |
| Extinction coefficient | 0.0146 (13) |
| Maximum difference (peak top and valley) | 0.820 and −0.632 e.A^−3 |

TABLE 4

Atomic Coordinate (×10$^4$) And Equivalent Isotropic Displacement Parameters (Å$^2$ × 10$^3$)

| | x | y | z | U(eq) |
|---|---|---|---|---|
| F(1) | 9368(2) | 4612(9) | 9653(3) | 96(2) |
| F(2) | 9372(4) | −803(11) | 10114(5) | 138(4) |
| F(3) | 5646(3) | −1481(11) | 5026(4) | 112(3) |
| F(4) | 5625(3) | −6934(12) | 5279(4) | 116(3) |
| F(5) | 7893(3) | 5997(8) | 3106(2) | 82(2) |
| F(6) | 7373(4) | 11325(9) | 3109(3) | 116(3) |
| F(7) | 7322(5) | 11609(14) | 11848(5) | 132(4) |
| F(8) | 7585(14) | 17130(20) | 11834(5) | 380(20) |
| O(1) | 6651(2) | 4283(8) | 8451(2) | 60(2) |
| O(2) | 6675(2) | 6199(7) | 7452(2) | 54(1) |
| O(3) | 5845(3) | 7708(7) | 7508(2) | 55(1) |
| O(4) | 6247(2) | 8326(7) | 6790(2) | 54(1) |
| O(5) | 6168(3) | 10927(8) | 6760(3) | 67(2) |
| O(6) | 6778(3) | 10655(8) | 8808(2) | 60(1) |
| O(7) | 6956(3) | 9715(10) | 8038(2) | 69(2) |
| O(8) | 8296(2) | −1320(8) | 6533(2) | 58(1) |
| O(9) | 8219(2) | 939(7) | 7503(3) | 56(1) |
| O(10) | 9082(3) | 2428(8) | 7476(2) | 58(1) |
| O(11) | 8640(3) | 3079(8) | 8162(2) | 57(1) |
| O(12) | 8740(3) | 5735(8) | 8172(3) | 74(2) |
| O(13) | 8222(3) | 5130(10) | 6143(3) | 73(2) |
| O(14) | 8004(3) | 4478(10) | 6908(3) | 73(2) |
| O(15) | 9066(3) | 6265(7) | 5810(2) | 55(1) |
| O(16) | 10055(2) | 4269(6) | 5779(2) | 51(1) |
| O(17) | 10692(2) | 2088(6) | 6223(2) | 50(1) |
| O(18) | 9969(2) | 2821(8) | 6614(3) | 57(1) |
| O(19) | 10686(3) | −517(7) | 6317(3) | 64(2) |
| O(20) | 9447(2) | 677(8) | 5531(2) | 59(2) |
| O(21) | 8678(2) | −204(9) | 5710(3) | 64(2) |
| O(22) | 5962(3) | 11902(8) | 9179(3) | 63(2) |
| O(23) | 4968(3) | 9978(7) | 9228(3) | 57(1) |
| O(24) | 5010(2) | 8456(7) | 8386(2) | 54(1) |
| O(25) | 4293(2) | 7827(6) | 8804(3) | 55(1) |
| O(26) | 4279(3) | 5206(8) | 8719(3) | 65(2) |
| O(27) | 5553(3) | 6442(8) | 9477(3) | 60(2) |
| O(28) | 6314(2) | 5540(8) | 9284(2) | 58(1) |
| N(1) | 8193(3) | 4700(12) | 9221(3) | 67(2) |
| N(2) | 7438(3) | 4033(10) | 8166(3) | 54(2) |
| N(3) | 6162(3) | 4232(10) | 6938(3) | 59(2) |
| N(4) | 6791(3) | −1236(11) | 5638(4) | 69(2) |
| N(5) | 7471(3) | −1324(10) | 6765(3) | 61(2) |
| N(6) | 8702(3) | −1036(9) | 8035(3) | 56(2) |
| N(7) | 8312(3) | 5888(9) | 4286(3) | 60(2) |
| N(8) | 9350(3) | 6468(8) | 5027(3) | 50(2) |
| N(9) | 10569(3) | 6218(9) | 6309(3) | 56(2) |
| N(10) | 6785(4) | 11547(12) | 10691(3) | 73(2) |
| N(11) | 5699(3) | 12142(8) | 9989(3) | 55(2) |
| N(12) | 4450(3) | 11940(9) | 8754(3) | 59(2) |
| B(1) | 6105(4) | 7039(11) | 7127(4) | 50(2) |
| B(2) | 8803(4) | 1700(11) | 7848(4) | 48(2) |
| B(3) | 10374(4) | 3452(10) | 6356(4) | 46(2) |
| B(4) | 4615(4) | 9203(11) | 8642(4) | 51(2) |
| C(1) | 8481(3) | 3305(12) | 9475(4) | 59(2) |
| C(2) | 9083(4) | 3250(14) | 9685(4) | 67(2) |
| C(3) | 9376(4) | 1868(15) | 9925(5) | 80(3) |
| C(4) | 9081(5) | 630(20) | 9908(7) | 106(5) |
| C(5) | 8497(5) | 584(13) | 9695(6) | 93(4) |
| C(6) | 8192(4) | 1870(14) | 9471(5) | 78(3) |
| C(7) | 8319(4) | 6268(13) | 9423(5) | 73(3) |
| C(8) | 7696(5) | 6690(15) | 9206(5) | 81(3) |
| C(9) | 7566(3) | 4865(12) | 9136(4) | 59(2) |
| C(10) | 7181(3) | 4391(11) | 8549(3) | 54(2) |

TABLE 4-continued

Atomic Coordinate (×10$^4$) And Equivalent Isotropic Displacement Parameters (Å$^2$ × 10$^3$)

| | x | y | z | U(eq) |
|---|---|---|---|---|
| C(11) | 7129(3) | 3604(12) | 7586(3) | 55(2) |
| C(12) | 6650(3) | 4677(11) | 7320(3) | 54(2) |
| C(13) | 5768(4) | 5506(10) | 6728(4) | 56(2) |
| C(14) | 5166(4) | 5019(10) | 6793(4) | 60(2) |
| C(15) | 4707(4) | 6257(12) | 6604(5) | 68(2) |
| C(16) | 4635(5) | 6937(17) | 5997(5) | 83(3) |
| C(17) | 4107(5) | 5545(19) | 6613(8) | 108(5) |
| C(18) | 6090(4) | 9721(10) | 6958(3) | 53(2) |
| C(19) | 5777(3) | 9377(10) | 7403(4) | 54(2) |
| C(20) | 5973(4) | 10402(12) | 7950(4) | 60(2) |
| C(21) | 6603(4) | 10189(11) | 8255(3) | 55(2) |
| C(22) | 6518(4) | −2717(14) | 5505(4) | 69(2) |
| C(23) | 5928(4) | −2760(14) | 5201(5) | 70(3) |
| C(24) | 5622(5) | −4268(17) | 5109(5) | 79(3) |
| C(25) | 5912(5) | −5524(15) | 5345(5) | 83(3) |
| C(26) | 6489(5) | −5569(16) | 5651(5) | 85(3) |
| C(27) | 6774(5) | −4101(14) | 5733(5) | 81(3) |
| C(28) | 6674(5) | 95(17) | 5218(6) | 94(4) |
| C(29) | 7320(5) | 560(20) | 5499(7) | 109(5) |
| C(30) | 7397(4) | −1038(15) | 5760(4) | 72(3) |
| C(31) | 7763(4) | −1238(11) | 6384(4) | 57(2) |
| C(32) | 7763(4) | −1661(11) | 7366(4) | 62(2) |
| C(33) | 8243(4) | −523(11) | 7630(3) | 54(2) |
| C(34) | 9119(4) | 271(13) | 8267(4) | 66(2) |
| C(35) | 9714(4) | −210(20) | 8258(5) | 99(5) |
| C(36) | 10216(9) | 680(40) | 8523(18) | 330(30) |
| C(37) | 10752(6) | −230(30) | 8618(16) | 280(20) |
| C(38) | 10185(9) | 1840(40) | 8832(9) | 196(14) |
| C(39) | 8831(4) | 4412(9) | 8003(4) | 52(2) |
| C(40) | 9161(3) | 4021(11) | 7573(3) | 52(2) |
| C(41) | 8995(3) | 5000(10) | 7038(3) | 49(2) |
| C(42) | 8367(4) | 4840(10) | 6703(4) | 53(2) |
| C(43) | 8043(4) | 7251(12) | 3986(4) | 61(2) |
| C(44) | 7837(4) | 7310(12) | 3399(4) | 65(2) |
| C(45) | 7611(4) | 8648(13) | 3096(4) | 69(2) |
| C(46) | 7573(5) | 9943(15) | 3400(5) | 84(3) |
| C(47) | 7790(6) | 10066(13) | 3988(4) | 80(3) |
| C(48) | 8029(5) | 8626(13) | 4294(4) | 69(2) |
| C(49) | 8084(5) | 4239(13) | 4140(4) | 74(3) |
| C(50) | 8288(5) | 3835(12) | 4776(4) | 72(3) |
| C(51) | 8381(4) | 5661(11) | 4889(4) | 61(2) |
| C(52) | 8962(4) | 6189(11) | 5285(3) | 54(2) |
| C(53) | 9938(4) | 6915(10) | 5352(3) | 51(2) |
| C(54) | 10200(3) | 5761(9) | 5831(3) | 47(2) |
| C(55) | 10786(4) | 4902(12) | 6706(4) | 57(2) |
| C(56) | 10742(5) | 5271(15) | 7309(4) | 73(3) |
| C(57) | 11251(10) | 5990(40) | 7716(8) | 88(8) |
| C(58) | 11223(15) | 5790(50) | 8325(10) | 124(14) |
| C(59) | 11168(14) | 7640(40) | 7510(20) | 170(20) |
| C(57A) | 11010(30) | 4140(80) | 7817(12) | 200(30) |
| C(58A) | 11330(30) | 3190(60) | 7833(12) | 270(50) |
| C(59A) | 10919(19) | 5060(50) | 8349(13) | 114(12) |
| C(60) | 10509(4) | 720(11) | 6414(4) | 58(2) |
| C(61) | 10067(3) | 1135(9) | 6693(3) | 49(2) |
| C(62) | 9522(4) | 168(11) | 6517(4) | 58(2) |
| C(63) | 9231(4) | 271(11) | 5880(4) | 59(2) |
| C(64) | 7006(4) | 12923(11) | 10959(4) | 61(2) |
| C(65) | 7260(6) | 12930(18) | 11552(5) | 90(4) |
| C(66) | 7481(11) | 14360(30) | 11853(6) | 156(9) |
| C(67) | 7433(13) | 15650(20) | 11540(8) | 177(12) |
| C(68) | 7208(14) | 15690(20) | 10948(9) | 237(18) |
| C(69) | 6970(7) | 14285(15) | 10690(5) | 98(4) |
| C(70) | 7033(7) | 10004(19) | 10826(5) | 103(5) |
| C(71) | 6765(6) | 9511(15) | 10165(4) | 83(3) |
| C(72) | 6663(4) | 11309(12) | 10059(4) | 61(2) |
| C(73) | 6084(4) | 11841(13) | 9701(4) | 62(2) |
| C(74) | 5126(4) | 12563(11) | 9695(3) | 55(2) |
| C(75) | 4833(4) | 11448(8) | 9211(4) | 49(2) |
| C(76) | 4226(4) | 10627(11) | 8322(4) | 60(2) |
| C(77) | 4263(5) | 11239(11) | 7726(4) | 69(2) |
| C(78) | 4065(5) | 9966(13) | 7265(5) | 78(3) |
| C(79) | 4098(7) | 10669(19) | 6685(7) | 113(5) |
| C(80) | 3484(6) | 9430(20) | 7201(6) | 111(5) |
| C(81) | 4460(3) | 6460(10) | 8636(3) | 51(2) |
| C(82) | 4893(3) | 6831(10) | 8297(4) | 50(2) |

TABLE 4-continued

Atomic Coordinate (×10⁴) And Equivalent Isotropic Displacement Parameters (Å 2 × 10³)

|        | x       | y        | z       | U(eq)  |
|--------|---------|----------|---------|--------|
| C(83)  | 5440(4) | 5829(12) | 8499(3) | 57(2)  |
| C(84)  | 5762(3) | 5993(10) | 9123(3) | 48(2)  |

The following target compounds (compound I-2 to compound I-10) were prepared by reference to the procedure of method 1 in step 7 of Example 4, wherein the compound 4-9 of method 1 in step 7 of Example 4 corresponds to compound b in Table 5 below, and L-malic acid of method 1 in step 7 of Example 4 corresponds to compound c in Table 5 below:

TABLE 5

| Compound number | Compound b | Compound c | Structure of target compound | ¹HNMR |
|---|---|---|---|---|
| I-2 | 4-9 | (structure) | (structure) | HNMR: ¹H NMR (400 MHz, DMSO-d₆) δ 10.83 (br s, 1H), 8.55 (br t, J = 5.90 Hz, 1H), 7.76 (br d, J = 6.78 Hz, 1H), 7.48 (br d, J = 7.28 Hz, 1H), 6.80-7.14 (m, 3H), 6.57-6.77 (m, 1H), 6.41 (br s, 1H), 4.37 (br t, J = 7.91 Hz, 1H), 4.10 (br d, J = 5.52 Hz, 2H), 3.78-3.96 (m, 1H), 3.64-3.75 (m, 1H), 2.71-2.94 (m, 1H), 2.09-2.30 (m, 2H), 1.57-1.76 (m, 1H), 1.28-1.51 (m, 2H), 0.78-0.98 (m, 6H). |
| I-3 | 4-9 | (structure) | (structure) | HNMR: ¹H NMR (400 MHz, DMSO-d₆) δ 10.27 (br s, 1H), 8.52 (t, J = 5.90 Hz, 1H), 7.10 (ddd, J = 2.76, 9.16, 12.42 Hz, 1H), 6.90 (dt, J = 1.63, 8.60 Hz, 1H), 6.46-6.63 (m, 1H), 4.44 (t, J = 7.65 Hz, 1H), 4.06 (br d, J = 6.02 Hz, 2H), 3.90-4.01 (m, 1H), 3.70-3.83 (m, 1H), 2.24-2.37 (m, 5H), 1.61 (td, J = 6.59, 13.43 Hz, 1H), 1.21-1.31 (m, 2H), 1.04-1.16 (m, 6H), 0.75-0.94 (m, 6H). |
| I-4 | 4-9 | (structure) | (structure) | ¹H NMR (400 MHz, DMSO-d6) δ 10.66 (br s, 1H), 8.57 (br t, J = 5.77 Hz, 1H), 7.11 (ddd, J = 2.76, 9.16, 12.42 Hz, 1H), 6.89 (br t, J = 7.65 Hz, 1H), 6.53 (dt, J = 5.77, 9.54 Hz, 1H), 4.44 (t, J = 7.91 Hz, 1H), 4.10 (br d, J = 5.77 Hz, 2H), 3.88-4.06 (m, 3H), 3.72-3.83 (m, 1H), 3.43 (dq, J = 5.02, 6.94 Hz, 1H), 2.65 (br d, J = 8.03 Hz, 1H), 2.28-2.41 (m, 1H), 1.59 (br s, 1H), 1.31 (br s, 2H), 0.85 (t, J = 6.53 Hz, 6H). |
| I-5 | 3-7 | (structure) | (structure) | ¹H NMR (400 MHz, DMSO-d6) δ 12.31 (br s, 1H), 10.69 (br s, 1H), 8.70 (br t, J = 5.90 Hz, 1H), 7.56 (dd, J = 1.51, 12.80 Hz, 1H), 7.44 (br d, J = 8.28 Hz, 1H), 6.55 (t, J = 8.66 Hz, 1H), 4.75 (br t, J = 6.78 Hz, 1H), 4.37 (dd, J = 3.89, 7.65 Hz, 1H), 4.11 (br d, J = 5.52 Hz, 3H), 3.93-4.03 (m, 1H), 2.61 (br d, J = 11.29 Hz, 3H), 2.19-2.44 (m, 2H), 1.53-1.70 (m, 1H), 1.21-1.35 (m, 2H), 0.74-0.93 (m, 6H). |

TABLE 5-continued

| Compound number | Compound b | Compound c | Structure of target compound | ¹HNMR |
|---|---|---|---|---|
| I-6 | 4-9 | (structure: (S)-2-hydroxy-3,3-dimethylbutanoic acid) | (target compound structure with 2,4-difluorophenyl azetidine, glycine, leucine boronate with t-butyl dioxaborolane) | ¹H NMR (400 MHz, DMSO-d6) δ 10.61 (br s, 1H), 8.56 (t, J = 5.90 Hz, 1H), 7.10 (ddd, J = 2.51, 9.29, 12.30 Hz, 1H), 6.84-7.00 (m, 1H), 6.46-6.63 (m, 1H), 4.45 (br t, J = 7.91 Hz, 1H), 3.89-4.22 (m, 3H), 3.63-3.82 (m, 2H), 2.56-2.70 (m, 1H), 2.25-2.40 (m, 2H), 1.62 (td, J = 6.43, 12.99 Hz, 1H), 1.21-1.38 (m, 2H), 0.77-0.97 (m, 15H). |
| I-7 | 4-9 | (structure: (S)-lactic acid) | (target compound structure with 2,4-difluorophenyl azetidine, glycine, leucine boronate with methyl dioxaborolane) | ¹H NMR (400 MHz, DMSO-d6) δ 10.61 (br s, 1H), 8.45-8.68 (m, 1H), 7.10 (ddd, J = 2.76, 9.22, 12.36 Hz, 1H), 6.89 (br t, J = 8.03 Hz, 1H), 6.44-6.66 (m, 1H), 4.44 (br t, J = 7.91 Hz, 1H), 4.02-4.24 (m, 3H), 3.89-4.02 (m, 1H), 3.64-3.82 (m, 1H), 2.62 (br t, J = 7.53 Hz, 1H), 2.26-2.41 (m, 2H), 1.59 (br s, 1H), 1.17-1.21 (m, 2H), 0.76-0.95 (m, 9H). |
| I-8 | 2-8 | (structure: (S)-malic acid) | (target compound structure with 3,5-difluoropyridyl azetidine, glycine, leucine boronate with carboxymethyl dioxaborolane) | ¹H NMR (400 MHz, DMSO-d6) δ 12.38 (br s, 1H), 10.64 (br s, 1H), 8.56 (br t, J = 5.40 Hz, 1H), 8.00 (d, J = 2.51 Hz, 1H), 7.71 (ddd, J = 2.51, 8.66, 11.42 Hz, 1H), 4.72 (br t, J = 7.91 Hz, 1H), 4.37 (dd, J = 3.89, 7.65 Hz, 1H), 4.26 (dd, J = 4.77, 7.78 Hz, 1H), 3.93-4.19 (m, 4H), 2.55-2.68 (m, 2H), 2.35 (br d, J = 7.53 Hz, 2H), 1.53-1.69 (m, 1H), 1.21-1.36 (m, 2H), 0.86 (t, J = 6.02 Hz, 6H). |
| I-9 | 2-9 | (structure: (S)-malic acid) | (target compound structure with trifluoromethyl thiazole azetidine, glycine, leucine boronate with carboxymethyl dioxaborolane) | ¹H NMR (400 MHz, DMSO-d6) δ 10.53-10.78 (m, 1H), 8.75-8.88 (m, 1H), 7.54-7.67 (m, 1H), 4.66-4.76 (m, 1H), 4.36 (dd, J = 3.89, 7.65 Hz, 1H), 4.10-4.20 (m, 2H), 3.93-4.06 (m, 2H), 2.56-2.73 (m, 3H), 2.31-2.46 (m, 2H), 1.62 (td, J = 6.59, 13.43 Hz, 1H), 1.21-1.32 (m, 2H), 0.81-0.92 (m, 6H). |
| I-10 | 1-9 | (structure: (S)-malic acid) | (target compound structure with 4-fluorophenyl azetidine, glycine, leucine boronate with carboxymethyl dioxaborolane) | ¹H NMR (400 MHz, DMSO-d6) δ 10.77 (br s, 1H), 8.84-9.02 (m, 1H), 6.94 (t, J = 8.91 Hz, 2H), 6.60 (br dd, J = 4.14, 7.65 Hz, 2H), 4.61 (dd, J = 5.40, 8.41 Hz, 1H), 4.29-4.39 (m, 1H), 4.22-4.30 (m, 1H), 4.10-4.19 (m, 2H), 2.54-2.66 (m, 2H), 2.14-2.31 (m, 2H), 1.98-2.10 (m, 1H), 1.56-1.69 (m, 1H), 1.21-1.34 (m, 2H), 0.79-0.91 (m, 6H). |

Experimental Example 1

In Vitro Anti-Proliferation Experiment for MM1.S Cells

In this experiment, the effect of compounds on inhibiting cell proliferation was investigated by determining their effect on cell activity in vitro in the tumor cell line MM1.S.

MM1.S cells were seeded into a black 96-well cell culture plate at a density of 7,000 cells per well, and the plates were then incubated overnight in an incubator at 37° C., 5% $CO_2$ and 100% relative humidity. Test compounds were added to the cell culture wells at a concentration (0.3 nM-2000 nM) and the plate was then put back into the incubator with vehicle control (DMSO added, no test compound) and blank control set. The plate was incubated for 2 days in an incubator at 37° C., 5% $CO_2$ and 100% relative humidity. Samples were processed using a standard method of the Promega CellTiter-Glo luminescence cell activity detection kit (Promega-G7571) and luminescence signals were detected on a SpectraMax i3× of Molecular Devices plate reader. The inhibition rate of the test compound was calculated using the following formula:

$$\text{Inhibition rate } \% = \frac{RLU \text{ vehicle control} - RLU \text{ compound}}{RLU \text{ vehicle control} - RLU \text{ blank control}} \times 100\%$$

The results are shown in Table 6.

TABLE 6

| Compound | IC$_{50}$ (µM) |
|---|---|
| I-1 | 0.0130 |
| 4-9 | 0.0010 |
| 3-7 | 0.0906 |
| 2-8 | 0.0240 |
| 2-9 | 0.0242 |
| 1-9 | 0.0058 |

Experimental Example 2: Liver Microsomal Stability Test for Compounds

Test compounds were each co-incubated with liver microsomes from CD-1 mice, SD rats, and humans to evaluate the stability of the test compounds.

Preparation of test compound solution samples: a 10 mM DMSO solution of the example compound (5 µL) was added to a mixed solvent of DMSO (45 µL), methanol and water (450 µL, volume ratio of methanol and water was 1:1) to prepare a 100 µM test compound solution; 50 µL of the 100 µM test compound solution was added to 450 µL of 100 mM potassium phosphate buffer to give a 10 µM test compound solution.

The 10 µM test compound solution was preincubated with microsomes of three species (human, rat and mouse, respectively) for 10 minutes, and then reduced nicotinamide adenine dinucleotide phosphate (NADPH) regeneration system working solution was added to the incubation plate according to each time point to initiate the reaction, and finally at 0, 5, 10, 20, 30 and 60 minutes, stop solution (100% ACN) was added to the reaction plate to stop the reaction. The test compounds were determined using LC-MS/MS method. The results of the liver microsomal stability test for the test compounds are shown in Table 7.

TABLE 7

| Compound | Liver microsomal stability (T$_{1/2}$, min) |
|---|---|
| 4-9 | 67.4(H), 43.1(R), 67.4(M) |
| 2-9 | 75.0(H), 26.5(R), 37.7(M) |
| 1-9 | 74.3(H), 42.1(R), 43.5(M) |

Note:
H stands for human, R stands for rat, and M stands for mouse.

Experimental Example 3: Cell Membrane Permeability Test for Compounds

Test compounds were evaluated for cell membrane permeability on MDR1-MDCK II cells.

Test compounds (10 mM DMSO solution of compound) were each diluted with transfer buffer (HBSS with 10 mM Hepes, pH=7.4) and formulated into samples at a final concentration of 2 µM, and then bidirectional (A-B and B-A) administration was performed. After administration, the cell plate was incubated for 150 minutes in an incubator at 37° C., 5% CO$_2$ and saturated humidity. After the 150 minutes of incubation, samples were collected and the concentrations of test compounds in the transfer samples were semi-quantitatively determined using LC-MS/MS method. The results of the cell membrane permeability test for the test compounds are shown in Table 8.

TABLE 8

| Compound | Papp A to B (10e−6 cm/s) | Papp B to A (10e−6 cm/s) | Efflux Ratio |
|---|---|---|---|
| 4-9 | 0.38 | 7.32 | 19.26 |
| 2-9 | 0.24 | 2.24 | 9.33 |

Note:
Papp A to B stands for the speed at which the compound enters into the cell; Papp B to A stands for the speed at which the cell secretes the compound; Efflux Ratio = Papp B to A/Papp A to B.

Experimental Example 4: Stability Experiment

About 50 mg of a sample was placed in a clean disposable petri dish and spread into a thin layer. The petri dish was covered with aluminum foil paper which was pricked with several small holes. The sample, in duplicate, was placed in stability boxes of 25° C.±2° C./60% RH±5% RH and 40° C.±2° C./75% RH±5% RH, respectively, and sampled at the planned time points, and the content of the compound was determined using the HPLC method, and the results are shown in Table 9.

TABLE 9

| Test compound | Conditions | Day 0 | Day 7 | Day 14 | Day 21 | Day 28 |
|---|---|---|---|---|---|---|
| I-1 | 25° C./60% | 98.6% | 97.8% | 100% | 100% | 100% |
|  | 40° C./75% | 98.6% | 99.1% | 98.5% | 100% | 100% |

What is claimed is:

1. A compound of formula (I), or a pharmaceutically acceptable salt thereof, a tautomer thereof, a stereoisomer thereof or a geometric isomer thereof:

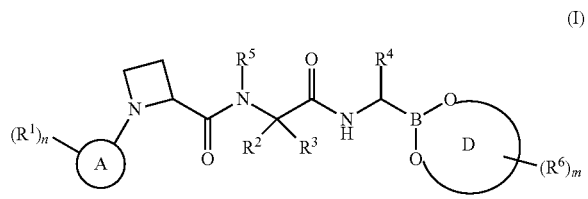

(I)

wherein,
ring A is selected from the group consisting of phenyl and 5-10 membered heteroaryl;
each $R^1$ is independently selected from the group consisting of halogen, CN, OH, NH$_2$, C$_{1-6}$ alkyl and C$_{1-6}$ heteroalkyl, wherein the C$_{1-6}$ alkyl or the C$_{1-6}$ heteroalkyl is optionally substituted by one or more groups selected from the group consisting of halogen, OH and NH$_2$;
n is selected from the group consisting of 0, 1, 2, 3, 4 and 5;
$R^2$ and $R^3$ are each independently selected from the group consisting of H and C$_{1-6}$ alkyl;
$R^4$ is selected from C$_{1-6}$ alkyl;
$R^5$ is selected from the group consisting of H and C$_{1-3}$ alkyl;
ring D is selected from 5-10 membered heterocyclyl, wherein the 5-10 membered heterocyclyl is substituted by at least one =O;
each $R^6$ is independently selected from the group consisting of halogen, OH, NH$_2$, COOH, C$_{1-6}$ alkyl, C$_{3-6}$ cycloalkyl, C$_{1-6}$ heteroalkyl, C$_{6-10}$ aryl and 5-10 membered heteroaryl, wherein the $C_{1-6}$ alkyl, $C_{3-6}$ cycloalkyl, $C_{1-6}$ heteroalkyl, $C_{6-10}$ aryl or 5-10 membered heteroaryl is optionally substituted by one or more groups selected from the group consisting of COOH, halogen, OH, $NH_2$ and SH; and m is selected from the group consisting of 0, 1, 2, 3, 4 and 5.

2. The compound of formula (I), or the pharmaceutically acceptable salt thereof, the tautomer thereof, the stereoisomer thereof or the geometric isomer thereof according to claim 1, wherein ring A is selected from the group consisting of phenyl and 5-6 membered heteroaryl, wherein the 5-6 membered heteroaryl contains at least one ring atom selected from the group consisting of nitrogen and sulfur.

3. The compound of formula (I), or the pharmaceutically acceptable salt thereof, the tautomer thereof, the stereoisomer thereof or the geometric isomer thereof according to claim 1, wherein, each $R^1$ is independently selected from the group consisting of halogen, CN, OH, $NH_2$, $C_{1-3}$ alkyl and $C_{1-3}$ alkoxy, wherein the $C_{1-3}$ alkyl or the $C_{1-3}$ alkoxy is optionally substituted by one or more groups selected from the group consisting of halogen, OH, and $NH_2$.

4. The compound of formula (I), or the pharmaceutically acceptable salt thereof, the tautomer thereof, the stereoisomer thereof or the geometric isomer thereof according to claim 1, wherein n is selected from the group consisting of 0, 1 and 2.

5. The compound of formula (I), or the pharmaceutically acceptable salt thereof, the tautomer thereof, the stereoisomer thereof or the geometric isomer thereof according to claim 1, wherein the structural unit

is selected from the group consisting of

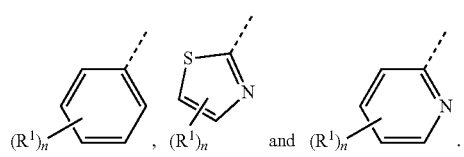

6. The compound of formula (I), or the pharmaceutically acceptable salt thereof, the tautomer thereof, the stereoisomer thereof or the geometric isomer thereof according to claim 1, wherein $R^2$ and $R^3$ are each independently selected from the group consisting of H and $C_{1-3}$ alkyl.

7. The compound of formula (I), or the pharmaceutically acceptable salt thereof, the tautomer thereof, the stereoisomer thereof or the geometric isomer thereof according to claim 1, wherein $R^4$ is selected from $C_{3-5}$ alkyl.

8. The compound of formula (I), or the pharmaceutically acceptable salt thereof, the tautomer thereof, the stereoisomer thereof or the geometric isomer thereof according to claim 1, wherein $R^5$ is selected from the group consisting of H and methyl.

9. The compound of formula (I), or the pharmaceutically acceptable salt thereof, the tautomer thereof, the stereoisomer thereof or the geometric isomer thereof according to claim 1, wherein, ring D is selected from 5-10 membered heterocyclyl, wherein the 5-10 membered heterocyclyl is substituted by one =O.

10. The compound of formula (I), or the pharmaceutically acceptable salt thereof, the tautomer thereof, the stereoisomer thereof or the geometric isomer thereof according to claim 1, wherein m is selected from the group consisting of 0, 1, 2 and 3.

11. The compound of formula (I), or the pharmaceutically acceptable salt thereof, the tautomer thereof, the stereoisomer thereof or the geometric isomer thereof according to claim 1, wherein each $R^6$ is independently selected from the group consisting of OH, $NH_2$, COOH and $C_{1-6}$ alkyl, wherein the $C_{1-6}$ alkyl is optionally substituted by one or more groups selected from the group consisting of COOH, OH and $NH_2$.

12. The compound of formula (I), or the pharmaceutically acceptable salt thereof, the tautomer thereof, the stereoisomer thereof or the geometric isomer thereof according to claim 1, wherein the structural unit

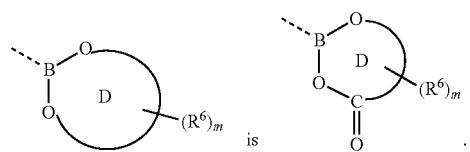

13. The compound of formula (I), or the pharmaceutically acceptable salt thereof, the tautomer thereof, the stereoisomer thereof or the geometric isomer thereof according to claim 1, wherein the compound of formula (I) is selected from the group consisting of a compound of formula (I-a), a compound of formula (II), a compound of formula (II-a), a compound of formula (III), a compound of formula (III-a), a compound of formula (IV) and a compound of formula (IV-a),

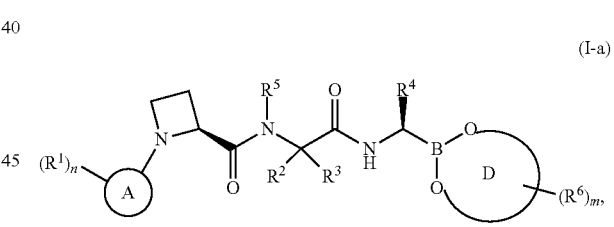
(I-a)

(II)

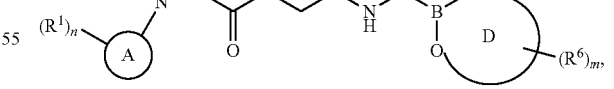
(II-a)

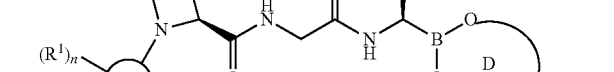

-continued (III)
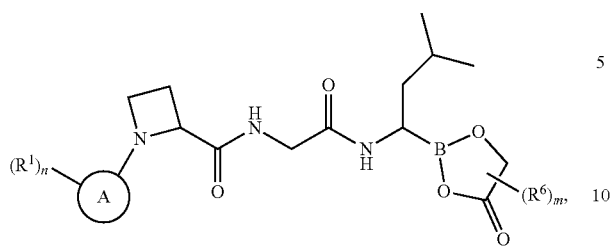

(III)
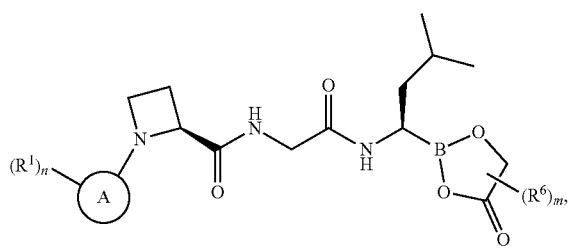

(IV)
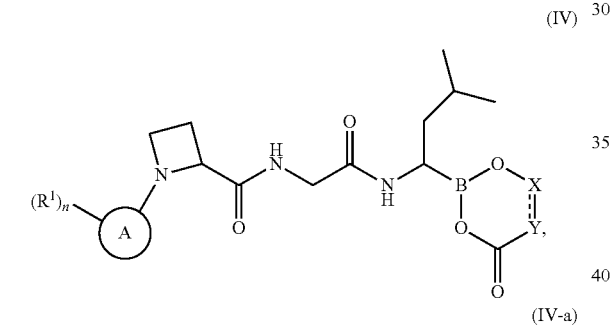

(IV-a)
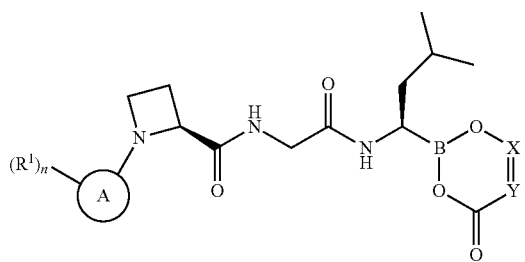

wherein X is selected from —C(R$^a$)$_2$— and Y is selected from —C(R$^b$)$_2$—; or X is selected from =C(R$^c$)— and Y is selected from =C(R$^d$)—, wherein R$^a$, R$^b$, R$^c$ and R$^d$ are each independently selected from the group consisting of hydrogen and C$_{1-6}$ alkyl, wherein the C$_{1-6}$ alkyl is optionally substituted by one or more —COOH, or R$^a$ and R$^b$ are connected to form a 3-6 membered ring, or R$^c$ and R$^d$ are connected to form a 3-6 membered ring.

14. The compound of formula (I), or the pharmaceutically acceptable salt thereof, the tautomer thereof, the stereoisomer thereof or the geometric isomer thereof according to claim 13, wherein the structural unit

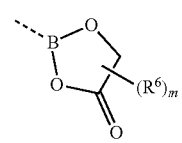

is selected from the group consisting of

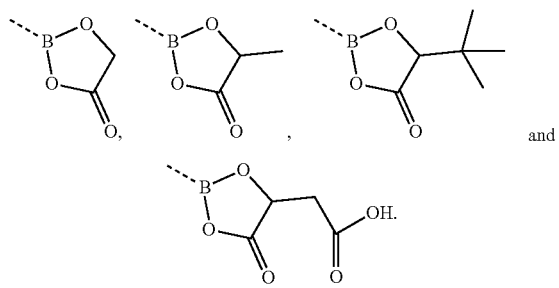

and

15. The compound of formula (I), or the pharmaceutically acceptable salt thereof, the tautomer thereof, the stereoisomer thereof or the geometric isomer thereof according to claim 1, being a compound selected from the group consisting of:

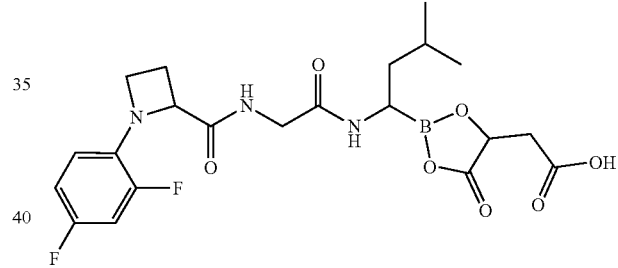

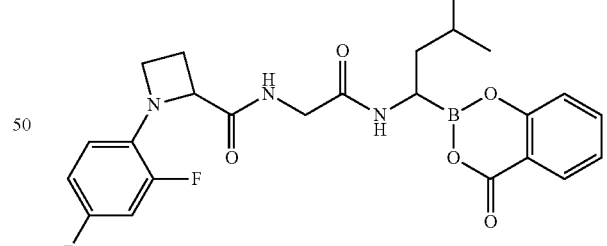

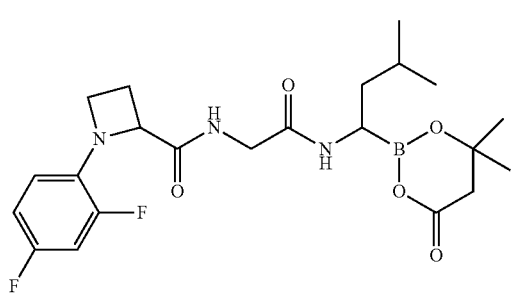

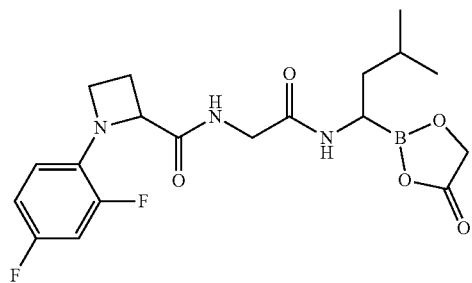
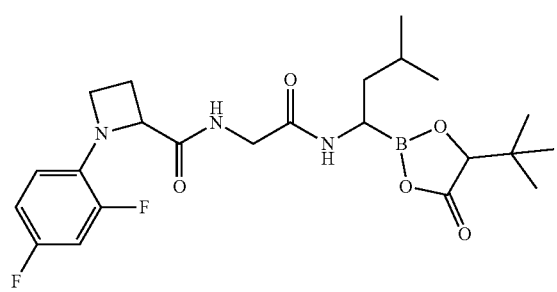
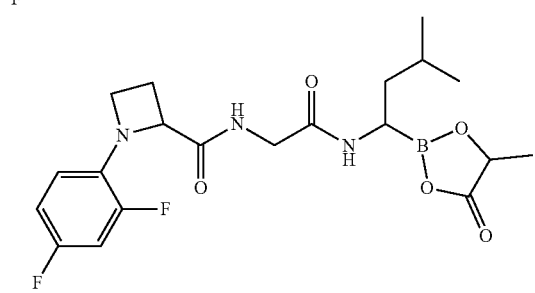
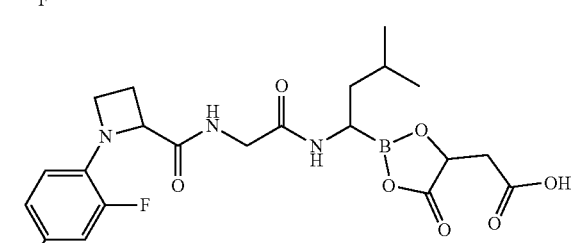
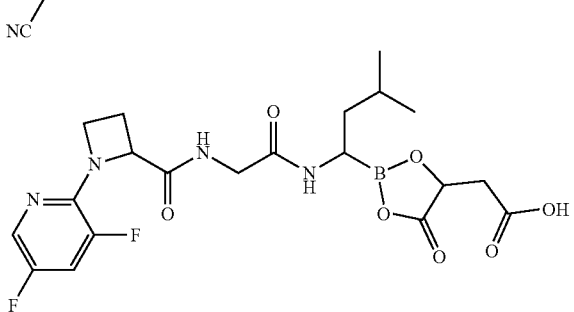
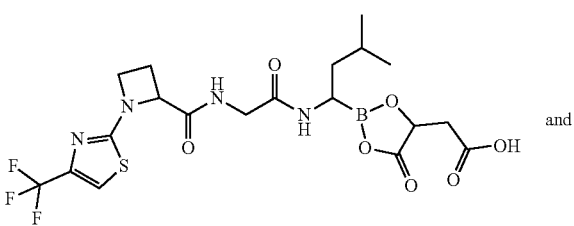
and
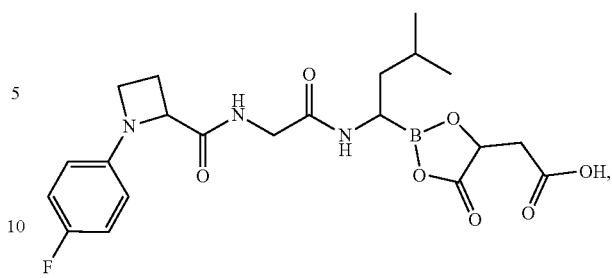
or a pharmaceutically acceptable salt thereof, a tautomer thereof, a stereoisomer thereof or a geometric isomer thereof.
16. The compound of formula (I), or the pharmaceutically acceptable salt thereof, the tautomer thereof, the stereoisomer thereof or the geometric isomer thereof according to claim 1, being a compound selected from the group consisting of:
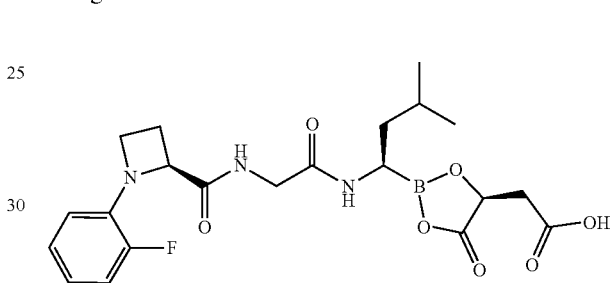
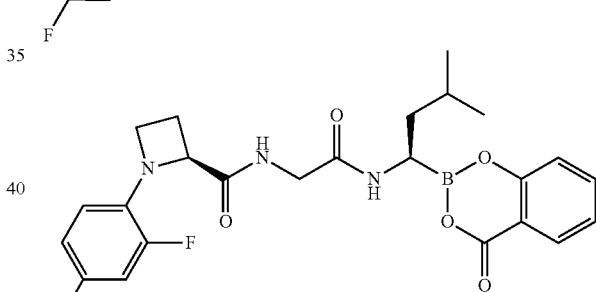
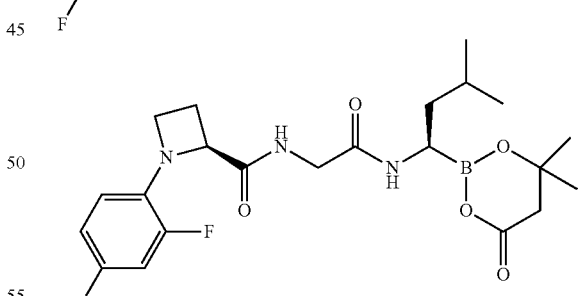
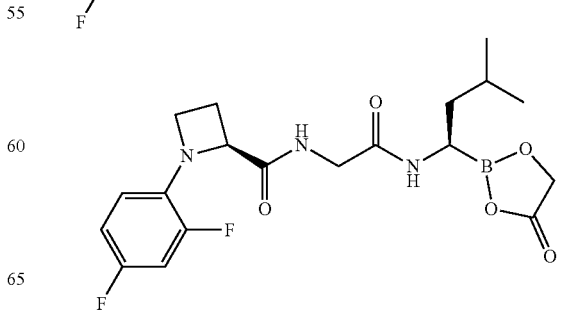

-continued

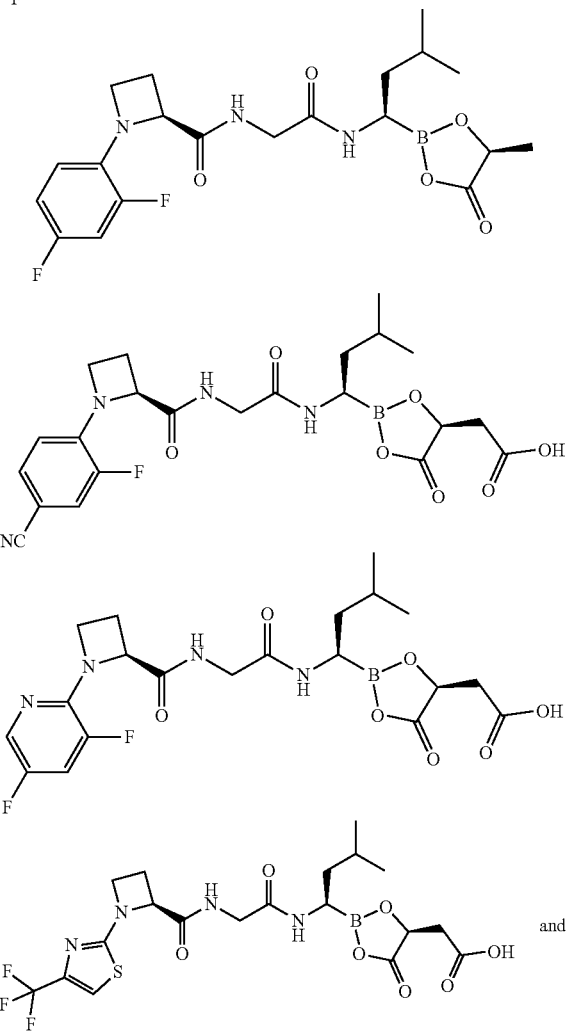

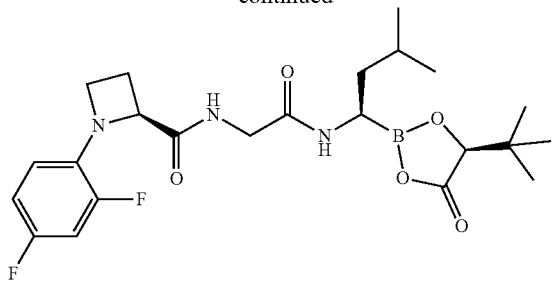

or a pharmaceutically acceptable salt thereof, a tautomer thereof or a geometric isomer thereof.

17. The compound of formula (I), or the pharmaceutically acceptable salt thereof, the tautomer thereof, the stereoisomer thereof or the geometric isomer thereof according to claim 1, wherein the compound is compound I-1, and wherein in the X-ray diffraction pattern using Cu-Kα ray, a crystal of compound I-1 has diffraction peaks at the following 2θ of 6.00, 11.98, 17.88, 20.88 and 21.48,

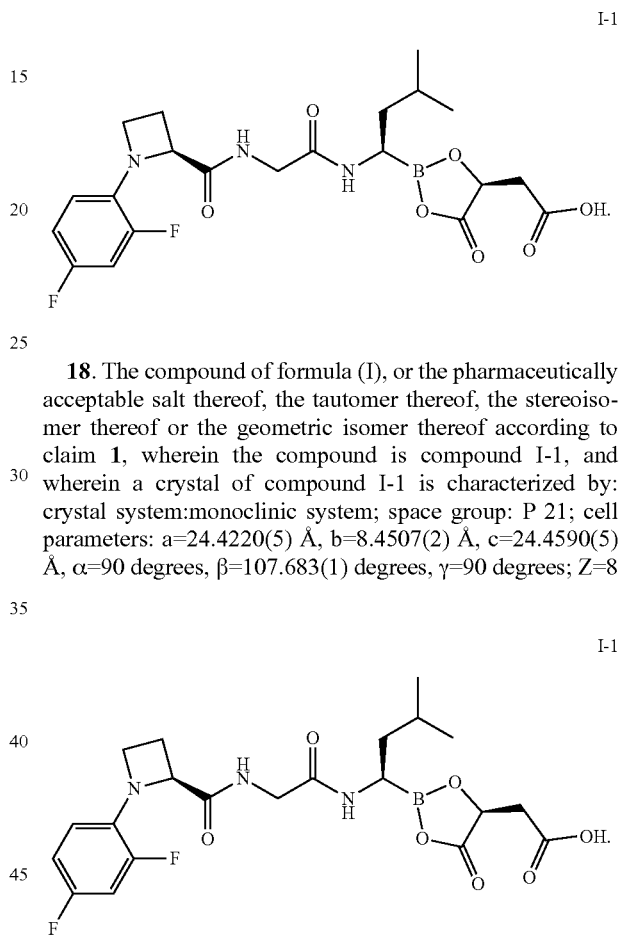

18. The compound of formula (I), or the pharmaceutically acceptable salt thereof, the tautomer thereof, the stereoisomer thereof or the geometric isomer thereof according to claim 1, wherein the compound is compound I-1, and wherein a crystal of compound I-1 is characterized by: crystal system:monoclinic system; space group: P 21; cell parameters: a=24.4220(5) Å, b=8.4507(2) Å, c=24.4590(5) Å, α=90 degrees, β=107.683(1) degrees, γ=90 degrees; Z=8

19. A pharmaceutical composition comprising the compound of formula (I), or the pharmaceutically acceptable salt thereof, the tautomer thereof, the stereoisomer thereof or the geometric isomer thereof according to claim 1.

20. A method for treating multiple myeloma in a mammal in need, comprising administering to the mammal a therapeutically effective amount of the compound of formula (I), or the pharmaceutically acceptable salt thereof, the tautomer thereof, the stereoisomer thereof or the geometric isomer thereof according to claim 1, or the pharmaceutical composition thereof.

* * * * *

UNITED STATES PATENT AND TRADEMARK OFFICE
CERTIFICATE OF CORRECTION

Page 1 of 2

PATENT NO. : 11,466,036 B2
APPLICATION NO. : 17/263476
DATED : October 11, 2022
INVENTOR(S) : Jian Xiong It is certified that error appears in the above-identified patent and that said Letters Patent is hereby corrected as shown below:

In the Specification

In Column 2, Line 18, delete "N2" and insert --$NH_2$--.

In Column 2, Lines 59-65, delete " 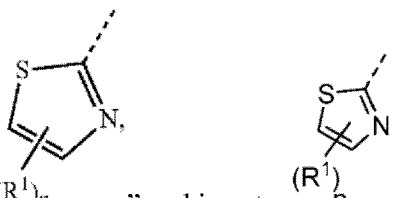 " and insert -- --.

In Column 6, Lines 56-58, delete " 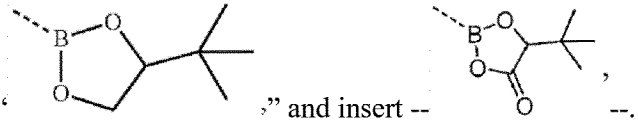 ," and insert -- --.

In Column 6, Lines 60-66, delete " 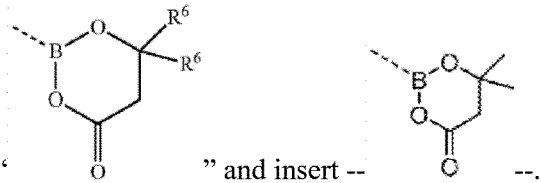 " and insert -- --.

In Column 12, Line 1, after "unit" insert -- 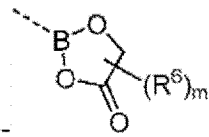 of the--.

In Column 22, Line 19, delete "20" and insert --2θ--.

In Column 22, Line 21, delete "20" and insert --2θ--.

Signed and Sealed this
Twenty-first Day of March, 2023

*Katherine Kelly Vidal*

Katherine Kelly Vidal
*Director of the United States Patent and Trademark Office*

CERTIFICATE OF CORRECTION (continued)
U.S. Pat. No. 11,466,036 B2

In Column 22, Line 24, delete "20" and insert --2θ--.

In Column 22, Line 27, delete "20" and insert --2θ--.

In Column 25, Line 59, delete "oxoazepinyl," and insert --oxazepinyl,--.

In Column 28, Line 23, delete "asymetrical" and insert --asymmetrical--.

In Column 31, Line 30-31, delete "N, N-" and insert --N,N- --.

In Column 31, Line 34, delete "THE" and insert --THF--.

In Column 36, Line 60, delete "THE" and insert --THF--.

In Column 37, Line 25, delete "THE" and insert --THF--.

In Column 43, Line 51, delete "m;" and insert --μm;--.

In Column 47, Line 14, delete "bin" and insert --b in--.

In Columns 47-48, Line 28 (TABLE 5), delete "-d6)" and insert -- -$d_6$)--.

In Columns 47-48, Line 41 (TABLE 5), delete "-d6)" and insert -- -$d_6$)--.

In Columns 49-50, Line 4 (TABLE 5-continued), delete "-d6)" and insert -- -$d_6$)--.

In Columns 49-50, Line 14 (TABLE 5-continued), delete "-d6)" and insert -- -$d_6$)--.

In Columns 49-50, Line 25 (TABLE 5-continued), delete "-d6)" and insert -- -$d_6$)--.

In Columns 49-50, Line 37 (TABLE 5-continued), delete "-d6)" and insert -- -$d_6$)--.

In Columns 49-50, Line 46 (TABLE 5-continued), delete "-d6)" and insert -- -$d_6$)--.

In the Claims

In Column 55, Claim 13, Line 16, delete "(III)" and insert --(III-a)--.